(12) United States Patent
Mathis et al.

(10) Patent No.: US 10,390,838 B1
(45) Date of Patent: Aug. 27, 2019

(54) TUNED STRENGTH CHRONIC OBSTRUCTIVE PULMONARY DISEASE TREATMENT

(71) Applicant: PneumRx, Inc., Santa Clara, CA (US)

(72) Inventors: Mark Mathis, Fremont, CA (US); Verna Rodriguez, Santa Cruz, CA (US)

(73) Assignee: PneumRx, Inc., Santa Clara, CA (US)

( * ) Notice: Subject to any disclaimer, the term of this patent is extended or adjusted under 35 U.S.C. 154(b) by 769 days.

(21) Appl. No.: 14/831,007

(22) Filed: Aug. 20, 2015

Related U.S. Application Data

(60) Provisional application No. 62/039,646, filed on Aug. 20, 2014.

(51) Int. Cl.
*A61B 1/04* (2006.01)
*A61B 17/12* (2006.01)
(Continued)

(52) U.S. Cl.
CPC ............ *A61B 17/1214* (2013.01); *A61B 5/08* (2013.01); *A61B 17/12036* (2013.01);
(Continued)

(58) Field of Classification Search
CPC .......... A61B 17/1214; A61B 17/12036; A61B 17/12104; A61B 5/08; A61B 2017/00867; A61B 2017/00809; A61B 2017/1205
See application file for complete search history.

(56) References Cited

U.S. PATENT DOCUMENTS

| | | | |
|---|---|---|---|
| 3,559,652 A | 2/1971 | Banitt et al. | |
| 4,013,080 A | 3/1977 | Froning | |
| 4,153,058 A | 5/1979 | Nehme | |
| 4,233,984 A | 11/1980 | Walling | |
| 4,245,624 A | 1/1981 | Komiya | |
| 4,479,792 A | 10/1984 | Lazarus et al. | |
| 4,494,531 A | 1/1985 | Gianturco | |
| 4,532,935 A | 8/1985 | Wang | |
| 4,702,260 A | 10/1987 | Wang | |
| 4,739,760 A | 4/1988 | Chin et al. | |

(Continued)

FOREIGN PATENT DOCUMENTS

| | | |
|---|---|---|
| CA | 2340376 A1 | 3/2000 |
| FR | 2840796 | 12/2003 |

(Continued)

OTHER PUBLICATIONS

Hermanson, Greg T. Bioconjugate Techniques. San Diego: Academic Press, Inc. 1996. (Table of contents only), 3 pages.
(Continued)

*Primary Examiner* — Ahn T Dang
(74) *Attorney, Agent, or Firm* — Kilpatrick Townsend and Stockton LLP

(57) ABSTRACT

The present invention generally provides improved medical devices, systems, and methods, particularly for treating one or both lungs of a patient with an implant, such as a coil, having a strength tuned to a patient's tissue treatment region. More particularly, embodiments of the present invention include a method for treating a lung of a patient with chronic obstructive pulmonary disease. The method comprises determining a regional tissue density of at least a portion of lung tissue of the patient and selecting between first and second coils based on the determined regional tissue density of the portion of lung tissue. In particular, the first coil has a first austenite final tuning and second coil has a second austenite final tuning different than the first tuning. Determining may comprise imaging at least the portion of lung tissue of the patient so as to identify a localized lung tissue density. Selecting may comprise matching the determined tissue density of the treatment region to a tuned strength of the first or second coil.

33 Claims, 15 Drawing Sheets

(51) Int. Cl.
*A61B 5/08* (2006.01)
*A61B 17/00* (2006.01)

(52) U.S. Cl.
CPC ............... *A61B 17/12104* (2013.01); *A61B 2017/00809* (2013.01); *A61B 2017/00867* (2013.01); *A61B 2017/1205* (2013.01)

(56) References Cited

U.S. PATENT DOCUMENTS

| | | |
|---|---|---|
| 4,766,906 A | 8/1988 | Wang |
| 4,769,017 A | 9/1988 | Fath et al. |
| 4,821,722 A | 4/1989 | Miller et al. |
| 4,880,015 A | 11/1989 | Nierman |
| 5,056,529 A | 10/1991 | de Groot |
| 5,084,012 A | 1/1992 | Kelman |
| 5,108,368 A | 4/1992 | Hammerslag et al. |
| 5,165,420 A | 11/1992 | Strickland |
| 5,186,167 A | 2/1993 | Kolobow |
| 5,190,546 A | 3/1993 | Jervis |
| 5,219,895 A | 6/1993 | Kelman |
| 5,240,011 A | 8/1993 | Assa |
| 5,261,889 A | 11/1993 | Laine et al. |
| 5,303,714 A | 4/1994 | Abele et al. |
| 5,312,329 A | 5/1994 | Beaty et al. |
| 5,312,331 A | 5/1994 | Knoepfler |
| 5,315,992 A | 5/1994 | Dalton |
| 5,334,183 A | 8/1994 | Wuchinich |
| 5,342,387 A | 8/1994 | Summers |
| 5,354,287 A | 10/1994 | Wacks |
| 5,385,606 A | 1/1995 | Kowanko |
| 5,423,830 A | 6/1995 | Schneebaum et al. |
| 5,472,017 A | 12/1995 | Kovalcheck |
| 5,479,938 A | 1/1996 | Weier |
| 5,484,401 A | 1/1996 | Rodriguez et al. |
| 5,514,536 A | 5/1996 | Taylor |
| 5,522,819 A | 6/1996 | Graves et al. |
| 5,526,821 A | 6/1996 | Jamshidi |
| 5,549,551 A | 8/1996 | Peacock, III et al. |
| 5,549,904 A | 8/1996 | Juergensen et al. |
| 5,599,294 A | 2/1997 | Edwards et al. |
| 5,660,175 A | 8/1997 | Dayal |
| 5,660,185 A | 8/1997 | Shmulewitz et al. |
| 5,697,365 A | 12/1997 | Pel |
| 5,735,264 A | 4/1998 | Siczek et al. |
| 5,736,132 A | 4/1998 | Juergensen et al. |
| 5,750,657 A | 5/1998 | Edwardson et al. |
| 5,762,070 A | 6/1998 | Nagamatsu |
| 5,846,235 A | 12/1998 | Pasricha et al. |
| 5,875,692 A | 3/1999 | Lin |
| 5,895,417 A | 4/1999 | Pomeranz et al. |
| 5,916,210 A | 6/1999 | Winston |
| 5,916,212 A | 6/1999 | Baust et al. |
| 5,938,635 A | 8/1999 | Kuhle |
| 5,954,636 A | 9/1999 | Schwartz et al. |
| 5,957,919 A | 9/1999 | Laufer |
| 5,964,770 A | 10/1999 | Flomenblit et al. |
| 5,972,026 A | 10/1999 | Laufer et al. |
| 5,978,697 A | 11/1999 | Maytal et al. |
| 6,063,111 A | 5/2000 | Hieshima et al. |
| 6,066,090 A | 5/2000 | Yoon |
| 6,080,113 A | 6/2000 | Heneveld et al. |
| 6,083,255 A | 7/2000 | Laufer et al. |
| 6,123,665 A | 9/2000 | Kawano |
| 6,174,323 B1 | 1/2001 | Biggs et al. |
| 6,183,498 B1 | 2/2001 | DeVore et al. |
| 6,196,966 B1 | 3/2001 | Kerin et al. |
| 6,200,333 B1 | 3/2001 | Laufer |
| 6,245,090 B1 | 6/2001 | Gilson et al. |
| 6,258,100 B1 | 7/2001 | Alferness et al. |
| 6,267,732 B1 | 7/2001 | Heneveld et al. |
| 6,273,907 B1 | 8/2001 | Laufer |
| 6,283,988 B1 | 9/2001 | Laufer et al. |
| 6,283,989 B1 | 9/2001 | Laufer et al. |
| 6,287,290 B1 | 9/2001 | Perkins et al. |
| 6,287,304 B1 | 9/2001 | Eggers et al. |
| 6,293,951 B1 | 9/2001 | Alferness et al. |
| 6,299,633 B1 | 10/2001 | Laufer |
| 6,306,141 B1 | 10/2001 | Jervis |
| 6,310,166 B1 | 10/2001 | Hickey et al. |
| 6,312,428 B1 | 11/2001 | Eggers et al. |
| 6,315,737 B1 | 11/2001 | Skinner |
| 6,328,689 B1 | 12/2001 | Gonzalez et al. |
| 6,328,701 B1 | 12/2001 | Terwilliger |
| 6,352,503 B1 | 3/2002 | Matsui et al. |
| 6,379,373 B1 | 4/2002 | Sawhney et al. |
| 6,387,044 B1 | 5/2002 | Tachibana et al. |
| 6,390,967 B1 | 5/2002 | Forman et al. |
| 6,398,775 B1 | 6/2002 | Perkins et al. |
| 6,402,701 B1 | 6/2002 | Kaplan et al. |
| 6,402,754 B1 | 6/2002 | Gonzalez |
| 6,402,781 B1 | 6/2002 | Langberg et al. |
| 6,411,852 B1 | 6/2002 | Danek et al. |
| 6,416,554 B1 | 7/2002 | Alferness et al. |
| 6,443,944 B1 | 9/2002 | Doshi et al. |
| 6,447,534 B2 | 9/2002 | Cragg et al. |
| 6,464,648 B1 | 10/2002 | Nakamura |
| 6,474,340 B1 | 11/2002 | Vaska et al. |
| 6,478,730 B1 | 11/2002 | Bala et al. |
| 6,485,407 B2 | 11/2002 | Alferness et al. |
| 6,485,436 B1 | 11/2002 | Truckai et al. |
| 6,488,673 B1 | 12/2002 | Laufer et al. |
| 6,491,706 B1 | 12/2002 | Alferness et al. |
| 6,494,844 B1 | 12/2002 | Van Bladel et al. |
| 6,494,897 B2 | 12/2002 | Sterman et al. |
| 6,509,031 B1 | 1/2003 | Miller et al. |
| 6,514,290 B1 | 2/2003 | Loomas |
| 6,514,522 B2 | 2/2003 | Domb |
| 6,527,761 B1 | 3/2003 | Soltesz et al. |
| 6,537,195 B2 | 3/2003 | Forman |
| 6,537,314 B2 | 3/2003 | Langberg et al. |
| 6,540,694 B1 | 4/2003 | Van Bladel et al. |
| 6,540,716 B1 | 4/2003 | Holm |
| 6,549,800 B1 | 4/2003 | Atalar et al. |
| 6,551,255 B2 | 4/2003 | Van Bladel et al. |
| 6,551,302 B1 | 4/2003 | Rosinko et al. |
| 6,552,172 B2 | 4/2003 | Marx et al. |
| 6,558,337 B2 | 5/2003 | Dvorak et al. |
| 6,568,387 B2 | 5/2003 | Davenport et al. |
| 6,569,166 B2 | 5/2003 | Gonzalez |
| 6,577,893 B1 | 6/2003 | Besson et al. |
| 6,585,639 B1 | 7/2003 | Kotmel et al. |
| 6,589,161 B2 | 7/2003 | Corcoran |
| 6,592,559 B1 | 7/2003 | Pakter et al. |
| 6,592,594 B2 | 7/2003 | Rimbaugh et al. |
| 6,599,311 B1 | 7/2003 | Biggs et al. |
| 6,610,043 B1 | 8/2003 | Ingenito |
| 6,622,731 B2 | 9/2003 | Daniel et al. |
| 6,629,951 B2 | 10/2003 | Laufer et al. |
| 6,632,222 B1 | 10/2003 | Edwards et al. |
| 6,632,239 B2 | 10/2003 | Snyder et al. |
| 6,632,243 B1 | 10/2003 | Zadno-Azizi et al. |
| 6,634,363 B1 | 10/2003 | Danek et al. |
| 6,638,275 B1 | 10/2003 | McGaffigan et al. |
| 6,645,205 B2 | 11/2003 | Ginn |
| 6,652,516 B1 | 11/2003 | Gough |
| 6,652,520 B2 | 11/2003 | Moorman et al. |
| 6,653,525 B2 | 11/2003 | Ingenito et al. |
| 6,663,624 B2 | 12/2003 | Edwards et al. |
| 6,679,264 B1 | 1/2004 | Deem et al. |
| 6,682,520 B2 | 1/2004 | Ingenito |
| 6,685,626 B2 | 2/2004 | Wironen |
| 6,689,072 B2 | 2/2004 | Kaplan et al. |
| 6,690,976 B2 | 2/2004 | Fenn et al. |
| 6,692,494 B1 | 2/2004 | Cooper et al. |
| 6,694,977 B1 | 2/2004 | Federowicz et al. |
| 6,694,979 B2 | 2/2004 | Deem et al. |
| 6,695,791 B2 | 2/2004 | Gonzalez |
| 6,709,401 B2 | 3/2004 | Perkins et al. |
| 6,709,408 B2 | 3/2004 | Fisher |
| 6,709,456 B2 | 3/2004 | Langberg et al. |
| 6,712,812 B2 | 3/2004 | Roschak et al. |
| 6,716,180 B2 | 4/2004 | Fontenot |
| 6,723,095 B2 | 4/2004 | Hammerslag |
| 6,730,044 B2 | 5/2004 | Stephens et al. |

(56) References Cited

U.S. PATENT DOCUMENTS

| | | |
|---|---|---|
| 6,736,822 B2 | 5/2004 | McClellan et al. |
| 6,749,606 B2 | 6/2004 | Keast et al. |
| 6,752,767 B2 | 6/2004 | Turovskiy et al. |
| 6,752,812 B1 | 6/2004 | Truwit |
| 6,758,824 B1 | 7/2004 | Miller et al. |
| 6,768,425 B2 | 7/2004 | Flaherty et al. |
| 6,770,066 B1 | 8/2004 | Weaver et al. |
| 6,770,070 B1 | 8/2004 | Balbierz |
| 6,789,545 B2 | 9/2004 | Littrup et al. |
| 6,790,172 B2 | 9/2004 | Alferness et al. |
| 6,790,185 B1 | 9/2004 | Fisher et al. |
| 6,797,001 B2 | 9/2004 | Mathis et al. |
| 6,807,446 B2 | 10/2004 | Fenn et al. |
| 6,808,525 B2 | 10/2004 | Latterell et al. |
| 6,814,778 B1 | 11/2004 | Farnworth |
| 6,817,973 B2 | 11/2004 | Merril et al. |
| 6,825,091 B2 | 11/2004 | Bae et al. |
| 6,827,086 B2 | 12/2004 | Shuman |
| 6,827,683 B2 | 12/2004 | Otawara |
| 6,830,756 B2 | 12/2004 | Hnojewyj |
| 6,840,243 B2 | 1/2005 | Deem et al. |
| 6,840,948 B2 | 1/2005 | Albrecht et al. |
| 6,840,952 B2 | 1/2005 | Saker et al. |
| 6,843,767 B2 | 1/2005 | Corcoran et al. |
| 6,849,262 B2 | 2/2005 | Ollerenshaw et al. |
| 6,852,108 B2 | 2/2005 | Barry et al. |
| 6,860,847 B2 | 3/2005 | Alferness et al. |
| 6,863,676 B2 | 3/2005 | Lee et al. |
| 6,875,209 B2 | 4/2005 | Zvuloni et al. |
| 6,878,106 B1 | 4/2005 | Herrmann |
| 6,878,141 B1 | 4/2005 | Perkins et al. |
| 6,886,558 B2 | 5/2005 | Tanaka |
| 6,901,927 B2 | 6/2005 | Deem et al. |
| 6,902,526 B2 | 6/2005 | Katzman |
| 6,902,536 B2 | 6/2005 | Manna et al. |
| 6,904,909 B2 | 6/2005 | Andreas et al. |
| 6,907,881 B2 | 6/2005 | Suki et al. |
| 6,908,440 B2 | 6/2005 | Fisher |
| 6,918,881 B2 | 7/2005 | Miller et al. |
| 6,929,637 B2 | 8/2005 | Gonzalez et al. |
| 6,936,014 B2 | 8/2005 | Vetter et al. |
| 6,941,950 B2 | 9/2005 | Wilson et al. |
| 6,942,627 B2 | 9/2005 | Huitema |
| 6,945,942 B2 | 9/2005 | Van Bladel et al. |
| 6,962,587 B2 | 11/2005 | Johnson et al. |
| 6,964,662 B2 | 11/2005 | Kidooka |
| 6,967,673 B2 | 11/2005 | Ozawa et al. |
| 6,979,344 B2 | 12/2005 | Jones et al. |
| 6,986,737 B2 | 1/2006 | Suzuki et al. |
| 6,997,189 B2 | 2/2006 | Biggs et al. |
| 6,997,918 B2 | 2/2006 | Soltesz et al. |
| 7,011,094 B2 | 3/2006 | Rapacki et al. |
| 7,022,088 B2 | 4/2006 | Keast et al. |
| 7,033,387 B2 | 4/2006 | Zadno-Azizi et al. |
| 7,036,509 B2 | 5/2006 | Rapacki et al. |
| 7,063,682 B1 | 6/2006 | Whayne et al. |
| 7,100,616 B2 | 9/2006 | Springmeyer |
| 7,112,225 B2 | 9/2006 | Ginn |
| 7,128,747 B2 | 10/2006 | Ginn |
| 7,141,046 B2 | 11/2006 | Perkins et al. |
| 7,165,548 B2 | 1/2007 | Deem et al. |
| 7,175,619 B2 | 2/2007 | Koblish et al. |
| 7,195,017 B2 | 3/2007 | Tanaka |
| 7,198,635 B2 | 4/2007 | Danek et al. |
| 7,300,428 B2 | 11/2007 | Ingenito |
| 7,351,202 B2 | 4/2008 | Long |
| 7,393,330 B2 | 7/2008 | Keast et al. |
| 7,393,363 B2 | 7/2008 | Ginn |
| 7,445,010 B2 | 11/2008 | Kugler et al. |
| 7,451,765 B2 | 11/2008 | Adler |
| 7,503,931 B2 | 3/2009 | Kowalsky et al. |
| 7,517,320 B2 | 4/2009 | Wibowo et al. |
| 7,549,984 B2 | 6/2009 | Mathis |
| 7,608,579 B2 | 10/2009 | Gong et al. |
| 7,662,181 B2 | 2/2010 | Deem et al. |
| 7,670,282 B2 | 3/2010 | Mathis |
| 7,731,651 B2 | 6/2010 | Pearce et al. |
| 7,757,691 B2 | 7/2010 | Reynolds et al. |
| 7,766,891 B2 | 8/2010 | McGurk et al. |
| 7,766,895 B2 | 8/2010 | Soltesz et al. |
| 7,766,938 B2 | 8/2010 | McGurk et al. |
| 7,775,968 B2 | 8/2010 | Mathis |
| 7,896,008 B2 | 3/2011 | Tanaka |
| 8,142,455 B2 | 3/2012 | Thompson et al. |
| 8,157,823 B2 | 4/2012 | Aronson et al. |
| 8,157,837 B2 | 4/2012 | Thompson et al. |
| 8,282,660 B2 | 10/2012 | Thompson et al. |
| 8,632,605 B2 | 1/2014 | Thompson et al. |
| 8,668,707 B2 | 3/2014 | Thompson et al. |
| 8,721,734 B2 | 5/2014 | Mathis et al. |
| 8,740,921 B2 | 6/2014 | Mathis et al. |
| 8,888,800 B2 | 11/2014 | Mathis et al. |
| 8,932,310 B2 | 1/2015 | Thompson et al. |
| 2001/0051799 A1 | 12/2001 | Ingenito |
| 2002/0007831 A1 | 1/2002 | Davenport et al. |
| 2002/0026188 A1 | 2/2002 | Balbierz et al. |
| 2002/0042564 A1 | 4/2002 | Cooper et al. |
| 2002/0042565 A1 | 4/2002 | Cooper et al. |
| 2002/0062120 A1 | 5/2002 | Perkins et al. |
| 2002/0077593 A1 | 6/2002 | Perkins et al. |
| 2002/0091379 A1 | 7/2002 | Danek et al. |
| 2002/0111620 A1 | 8/2002 | Cooper et al. |
| 2002/0112729 A1 | 8/2002 | DeVore et al. |
| 2002/0128647 A1 | 9/2002 | Roschak et al. |
| 2002/0138074 A1 | 9/2002 | Keast et al. |
| 2002/0161392 A1 | 10/2002 | Dubrul |
| 2002/0161399 A1 | 10/2002 | Cruise et al. |
| 2002/0176893 A1 | 11/2002 | Wironen et al. |
| 2002/0183244 A1 | 12/2002 | Ollerenshaw et al. |
| 2002/0183838 A1 | 12/2002 | Liddicoat et al. |
| 2002/0188171 A1 | 12/2002 | Alferness et al. |
| 2003/0018318 A1 | 1/2003 | Melsky |
| 2003/0029452 A1 | 2/2003 | Suki et al. |
| 2003/0050648 A1 | 3/2003 | Alferness et al. |
| 2003/0051733 A1 | 3/2003 | Kotmel et al. |
| 2003/0055331 A1 | 3/2003 | Kotmel et al. |
| 2003/0069488 A1 | 4/2003 | Alferness et al. |
| 2003/0070676 A1 | 4/2003 | Cooper et al. |
| 2003/0070682 A1 | 4/2003 | Wilson et al. |
| 2003/0070683 A1 | 4/2003 | Deem et al. |
| 2003/0075170 A1 | 4/2003 | Deem et al. |
| 2003/0083671 A1 | 5/2003 | Rimbaugh et al. |
| 2003/0083692 A1 | 5/2003 | Vrba et al. |
| 2003/0088195 A1 | 5/2003 | Vardi et al. |
| 2003/0100921 A1 | 5/2003 | Addis et al. |
| 2003/0109866 A1 | 6/2003 | Edwards et al. |
| 2003/0127090 A1 | 7/2003 | Gifford et al. |
| 2003/0130657 A1 | 7/2003 | Tom et al. |
| 2003/0154988 A1 | 8/2003 | DeVore et al. |
| 2003/0158515 A1 | 8/2003 | Gonzalez et al. |
| 2003/0159700 A1 | 8/2003 | Laufer et al. |
| 2003/0181356 A1 | 9/2003 | Ingenito |
| 2003/0181922 A1 | 9/2003 | Alferness |
| 2003/0183235 A1 | 10/2003 | Rimbaugh et al. |
| 2003/0191496 A1 | 10/2003 | Edwards et al. |
| 2003/0192551 A1 | 10/2003 | Deem et al. |
| 2003/0195385 A1 | 10/2003 | DeVore |
| 2003/0195511 A1 | 10/2003 | Barry |
| 2003/0212337 A1 | 11/2003 | Sirokman |
| 2003/0212412 A1 | 11/2003 | Dillard et al. |
| 2003/0212450 A1 | 11/2003 | Schlick |
| 2003/0233099 A1 | 12/2003 | Danaek et al. |
| 2004/0010209 A1 | 1/2004 | Sirokman |
| 2004/0010289 A1 | 1/2004 | Biggs et al. |
| 2004/0024356 A1 | 2/2004 | Tanaka |
| 2004/0030262 A1 | 2/2004 | Fisher et al. |
| 2004/0031494 A1 | 2/2004 | Danek et al. |
| 2004/0034357 A1 | 2/2004 | Beane et al. |
| 2004/0038868 A1 | 2/2004 | Ingenito |
| 2004/0040555 A1 | 3/2004 | Tanaka |
| 2004/0049187 A1 | 3/2004 | Burnett et al. |
| 2004/0049264 A1 | 3/2004 | Sowinski et al. |
| 2004/0052850 A1 | 3/2004 | Schankereli |
| 2004/0055606 A1 | 3/2004 | Hendricksen et al. |

(56) References Cited

U.S. PATENT DOCUMENTS

| | | |
|---|---|---|
| 2004/0059263 A1 | 3/2004 | De Vore et al. |
| 2004/0063613 A1 | 4/2004 | Rolke et al. |
| 2004/0072756 A1 | 4/2004 | Wilkie et al. |
| 2004/0073155 A1 | 4/2004 | Laufer et al. |
| 2004/0073191 A1 | 4/2004 | Soltesz et al. |
| 2004/0073201 A1 | 4/2004 | Cooper et al. |
| 2004/0073207 A1 | 4/2004 | Ginn |
| 2004/0073241 A1 | 4/2004 | Barry et al. |
| 2004/0078054 A1 | 4/2004 | Biggs et al. |
| 2004/0081676 A1 | 4/2004 | Schankereli et al. |
| 2004/0087886 A1 | 5/2004 | Gellman |
| 2004/0120849 A1 | 6/2004 | Stewart et al. |
| 2004/0133168 A1 | 7/2004 | Salcudean et al. |
| 2004/0134487 A1 | 7/2004 | Deem et al. |
| 2004/0154621 A1 | 8/2004 | Deem et al. |
| 2004/0158228 A1 | 8/2004 | Perkins |
| 2004/0162110 A1 | 8/2004 | Neuhaus et al. |
| 2004/0172058 A1 | 9/2004 | Edwards et al. |
| 2004/0176801 A1 | 9/2004 | Edwards et al. |
| 2004/0176833 A1 | 9/2004 | Pavenik et al. |
| 2004/0210248 A1 | 10/2004 | Gordon et al. |
| 2004/0211434 A1 | 10/2004 | Loomas et al. |
| 2004/0220556 A1 | 11/2004 | Cooper et al. |
| 2004/0225254 A1 | 11/2004 | Tanaka et al. |
| 2004/0231674 A1 | 11/2004 | Tanaka |
| 2004/0234575 A1 | 11/2004 | Horres et al. |
| 2004/0237966 A1 | 12/2004 | Tanaka |
| 2004/0244802 A1 | 12/2004 | Tanaka |
| 2004/0244803 A1 | 12/2004 | Tanaka |
| 2004/0267277 A1 | 12/2004 | Zannis et al. |
| 2005/0004599 A1 | 1/2005 | McNally-Heintzelman et al. |
| 2005/0015106 A1 | 1/2005 | Perkins et al. |
| 2005/0016530 A1 | 1/2005 | McCutcheon et al. |
| 2005/0033310 A1 | 2/2005 | Alferness et al. |
| 2005/0033344 A1 | 2/2005 | Dillard et al. |
| 2005/0043751 A1 | 2/2005 | Phan et al. |
| 2005/0043752 A1 | 2/2005 | Phan et al. |
| 2005/0049615 A1 | 3/2005 | Cooper et al. |
| 2005/0051163 A1 | 3/2005 | Deem et al. |
| 2005/0056292 A1 | 3/2005 | Cooper |
| 2005/0060041 A1 | 3/2005 | Phan et al. |
| 2005/0060042 A1 | 3/2005 | Phan et al. |
| 2005/0060044 A1 | 3/2005 | Roschak et al. |
| 2005/0061322 A1 | 3/2005 | Freitag |
| 2005/0085801 A1 | 4/2005 | Cooper et al. |
| 2005/0096529 A1 | 5/2005 | Cooper et al. |
| 2005/0101836 A1 | 5/2005 | Onuki et al. |
| 2005/0103340 A1 | 5/2005 | Wondka |
| 2005/0107783 A1 | 5/2005 | Tom et al. |
| 2005/0119614 A1 | 6/2005 | Melsky |
| 2005/0131339 A1 | 6/2005 | Makin et al. |
| 2005/0137518 A1 | 6/2005 | Biggs et al. |
| 2005/0137611 A1 | 6/2005 | Escudero et al. |
| 2005/0137712 A1 | 6/2005 | Biggs et al. |
| 2005/0137715 A1 | 6/2005 | Phan et al. |
| 2005/0145253 A1 | 7/2005 | Wilson et al. |
| 2005/0148902 A1 | 7/2005 | Minar et al. |
| 2005/0165328 A1 | 7/2005 | Heske et al. |
| 2005/0166925 A1 | 8/2005 | Wilson et al. |
| 2005/0171396 A1 | 8/2005 | Pankratov et al. |
| 2005/0177144 A1 | 8/2005 | Phan et al. |
| 2005/0178389 A1 | 8/2005 | Shaw et al. |
| 2005/0192526 A1 | 9/2005 | Biggs et al. |
| 2005/0196344 A1 | 9/2005 | McCutcheon et al. |
| 2005/0240277 A1 | 10/2005 | Aliski et al. |
| 2005/0244401 A1 | 11/2005 | Ingenito |
| 2005/0281739 A1 | 12/2005 | Gong et al. |
| 2005/0281740 A1 | 12/2005 | Gong et al. |
| 2005/0281796 A1 | 12/2005 | Gong et al. |
| 2005/0281797 A1 | 12/2005 | Gong et al. |
| 2005/0281798 A1 | 12/2005 | Gong et al. |
| 2005/0281799 A1 | 12/2005 | Gong et al. |
| 2005/0281800 A1 | 12/2005 | Gong et al. |
| 2005/0281801 A1 | 12/2005 | Gong et al. |
| 2005/0281802 A1 | 12/2005 | Gong et al. |
| 2005/0282748 A1 | 12/2005 | Gong et al. |
| 2005/0288549 A1 | 12/2005 | Mathis |
| 2005/0288550 A1 | 12/2005 | Mathis |
| 2005/0288684 A1 | 12/2005 | Aronson et al. |
| 2005/0288702 A1 | 12/2005 | McGurk et al. |
| 2006/0004305 A1 | 1/2006 | George et al. |
| 2006/0004388 A1 | 1/2006 | Whayne et al. |
| 2006/0004400 A1 | 1/2006 | McGurk et al. |
| 2006/0009748 A1 | 1/2006 | Mathis |
| 2006/0009801 A1 | 1/2006 | McGurk et al. |
| 2006/0020243 A1 | 1/2006 | Speck et al. |
| 2006/0025815 A1 | 2/2006 | McGurk et al. |
| 2006/0029548 A1 | 2/2006 | Pelleg et al. |
| 2006/0030863 A1 | 2/2006 | Fields et al. |
| 2006/0032497 A1 | 2/2006 | Doshi |
| 2006/0076023 A1 | 4/2006 | Rapacki et al. |
| 2006/0095002 A1 | 5/2006 | Soltesz et al. |
| 2006/0100666 A1 | 5/2006 | Wilkinson et al. |
| 2006/0116749 A1 | 6/2006 | Willink et al. |
| 2006/0118126 A1 | 6/2006 | Tanaka |
| 2006/0124126 A1 | 6/2006 | Tanaka |
| 2006/0135947 A1 | 6/2006 | Soltesz et al. |
| 2006/0135984 A1 | 6/2006 | Kramer et al. |
| 2006/0162731 A1 | 7/2006 | Wondka et al. |
| 2006/0167416 A1 | 7/2006 | Mathis et al. |
| 2006/0184016 A1 | 8/2006 | Glossop |
| 2006/0200076 A1 | 9/2006 | Gonzalez et al. |
| 2006/0206147 A1 | 9/2006 | DeVore et al. |
| 2006/0229528 A1 | 10/2006 | Heske et al. |
| 2006/0235432 A1 | 10/2006 | DeVore et al. |
| 2006/0235467 A1 | 10/2006 | DeVore et al. |
| 2006/0249164 A1 | 11/2006 | Springmeyer |
| 2006/0264772 A1 | 11/2006 | Aljuri et al. |
| 2006/0276807 A1 | 12/2006 | Keast et al. |
| 2006/0280772 A1 | 12/2006 | Roschak et al. |
| 2006/0280773 A1 | 12/2006 | Roschak et al. |
| 2006/0283462 A1 | 12/2006 | Fields et al. |
| 2007/0005083 A1 | 1/2007 | Sabanathan et al. |
| 2007/0096048 A1 | 5/2007 | Clerc |
| 2007/0185572 A1 | 8/2007 | Solem et al. |
| 2007/0221230 A1 | 9/2007 | Thompson et al. |
| 2008/0036763 A1 | 2/2008 | Chen et al. |
| 2008/0063693 A1 | 3/2008 | Cook |
| 2008/0161865 A1 | 7/2008 | Hagen |
| 2008/0183204 A1 | 7/2008 | Greenhalgh et al. |
| 2008/0200797 A1 | 8/2008 | Kotmel et al. |
| 2008/0262473 A1 | 10/2008 | Kornblau et al. |
| 2009/0012626 A1 | 1/2009 | Thompson et al. |
| 2009/0076526 A1 | 3/2009 | Rousseau et al. |
| 2009/0104183 A1 | 4/2009 | Gong et al. |
| 2009/0221967 A1 | 9/2009 | Thommen et al. |
| 2009/0306644 A1 | 12/2009 | Mayse et al. |
| 2010/0070050 A1* | 3/2010 | Mathis ............ A61B 17/12022 623/23.65 |
| 2010/0297218 A1 | 11/2010 | Gong et al. |
| 2012/0123514 A1 | 5/2012 | Kunis |
| 2012/0172909 A1 | 7/2012 | Mathis et al. |
| 2013/0096603 A1 | 4/2013 | Mathis et al. |
| 2013/0102887 A1 | 4/2013 | Thompson et al. |
| 2013/0103059 A1 | 4/2013 | Mathis et al. |
| 2013/0217956 A1 | 8/2013 | Thompson et al. |
| 2014/0188246 A1 | 7/2014 | Aronson et al. |
| 2014/0213958 A1* | 7/2014 | Clauson ............ A61F 9/00781 604/8 |
| 2014/0371705 A1 | 12/2014 | Mathis |
| 2015/0051709 A1 | 2/2015 | Vasquez et al. |
| 2015/0057695 A1 | 2/2015 | Mathis et al. |
| 2015/0073563 A1 | 3/2015 | Mathis et al. |

FOREIGN PATENT DOCUMENTS

| | | |
|---|---|---|
| GB | 2324729 A | 1/2002 |
| JP | H04-22908 | 2/1992 |
| JP | H10-5343 | 1/1998 |
| JP | 2005-287568 | 10/2005 |
| WO | 94/01508 A1 | 1/1994 |
| WO | 98/01084 A1 | 4/1998 |
| WO | 98/23227 | 6/1998 |
| WO | 01/13839 A1 | 3/2001 |

(56) References Cited

FOREIGN PATENT DOCUMENTS

| WO | 01/54618 A1 | 8/2001 |
|---|---|---|
| WO | 02/00270 A1 | 1/2002 |
| WO | 02/00275 A1 | 1/2002 |
| WO | 02/02158 A1 | 1/2002 |
| WO | 02/49554 A1 | 6/2002 |
| WO | 2003/022221 A1 | 3/2003 |
| WO | 03/028522 A2 | 4/2003 |
| WO | 2004/049970 A2 | 6/2004 |
| WO | 2004/062505 A1 | 7/2004 |
| WO | 2004/080347 A2 | 9/2004 |
| WO | 2005/058206 A1 | 6/2005 |
| WO | 2005/122870 A2 | 12/2005 |
| WO | 2007/016409 A1 | 2/2007 |
| WO | 2007/106495 A2 | 9/2007 |
| WO | 2008/036763 A2 | 3/2008 |
| WO | 2014/151557 A2 | 9/2014 |

OTHER PUBLICATIONS

LAM, et al. X-Ray Diagnosis: A Physician's Approach. Singapore: Springer. 1998. (Table of contents only), 6 pages.

O'Brien et al. "Improvements in Lung Function, Exercise, and Quality of Life in Hypercapnic COPD Patients After Lung Volume Reduction Surgery". Chest 115 (1999): 75-84, 10 pages.

Quint et al. "Diaphragmetic Shape Change After Lung Volume Reduction Surgery". Journal of Thoracic Imaging 16 (2001):149-155, 7 pages.

Rowe, et al. Handbook of Pharmaceutical Excipients. 4th Edition. London: Pharmaceutical Press. 2003. (Table of contents only), 6 pages.

Slone, et al. Body CT: A Practical Approach. New York: McGraw-Hill. 2000. (Table of contents only), 4 pages.

Stout, et al. X-Ray Structure Determination: A Practical Guide. 2nd Edition. New York: John Wiley & Sons. 1989. (Table of contents only), 9 pages.

The United States Pharmacopeia. 29th Revision. 2006. The United States Pharmacopeia Convention. Rockville, MD. (Table of contents only), 4 pages.

U.S. Appl. No. 60/885,305, filed Jan. 17, 2007; first named inventor: David Thompson, 70 pages.

Wkipedia, "Medical Ventilator", downloaded from Internet http://en/wikipedia.org/w/index.php?title+Medical_vntilator&printalbe=yes on Jan. 16, 2015, 5 pages.

Yusen et al. "A Prospective Evaluation of Lung Volume Reduction Surgery in 200 Consecutive Patients." Chest 123 (2003):1026-1037, 12 pages.

* cited by examiner

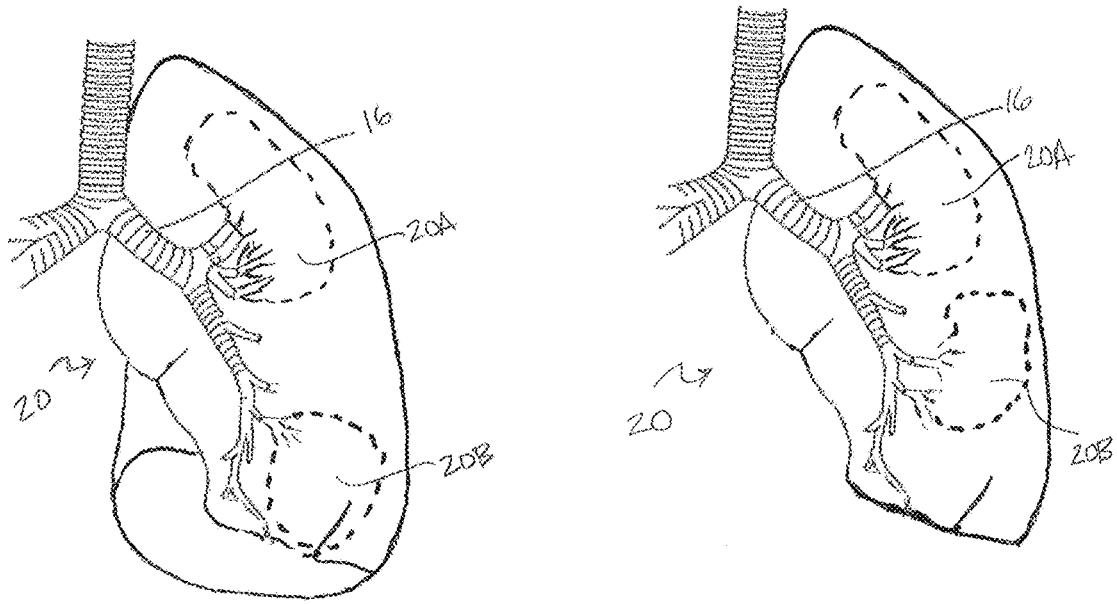
FIG. 12A
FIG. 12B
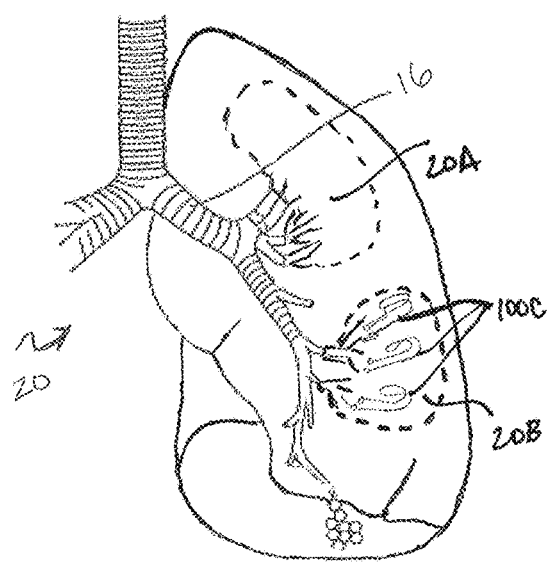
FIG. 12C

TUNED STRENGTH CHRONIC OBSTRUCTIVE PULMONARY DISEASE TREATMENT

CROSS-REFERENCES TO RELATED APPLICATIONS

This application claims priority to and the benefit of U.S. Provisional Patent Application No. 62/039,646 filed Aug. 20, 2014, the contents of which are incorporated herein by reference in their entirety.

This application is generally related to U.S. patent application Ser. No. 14/209,194 filed on Mar. 13, 2014, entitled Torque Alleviating Intra-Airway Lung Volume Reduction Compressive Implant Structures, which claims the benefit under 35 USC 119(e) of U.S. Provisional Application No. 61/791,517 filed Mar. 15, 2013, each of which are incorporated herein by reference in their entirety.

This application is generally related to U.S. patent application Ser. No. 12/782,515 filed on May 18, 2010 (now U.S. Pat. No. 8,721,734), entitled Cross-Sectional Modification During Deployment of an Elongate Lung Volume Reduction Device, which claims the benefit under 35 USC 119(e) of U.S. Provisional Application No. 61/179,306 filed May 18, 2009, each of which are incorporated herein by reference in their entirety.

This application is also generally related to U.S. patent application Ser. No. 12/167,167 filed on Jul. 2, 2008 (now U.S. Pat. No. 8,282,660), entitled Minimally Invasive Lung Volume Reduction Devices, Methods, and Systems, which is a continuation application of PCT Patent Application No. PCT/US07/06339 filed internationally on Mar. 13, 2007, which is a continuation-in-part of U.S. patent application Ser. No. 11/422,047 filed Jun. 2, 2006 (now U.S. Pat. No. 8,157,837), entitled Minimally Invasive Lung Volume Reduction Device and Method, each of which are incorporated herein by reference in their entirety.

This application is also generally related to U.S. Provisional Patent Applications 60/743,471 filed on Mar. 13, 2006; entitled Minimally Invasive Lung Volume Reduction Device and Method; 60/884,804 filed Jan. 12, 2007 entitled Minimally Invasive Lung Volume Reduction Devices, Methods and Systems; and 60/885,305 filed Jan. 17, 2007, entitled Minimally Invasive Lung Volume Reduction Devices, Methods and Systems, each of which are incorporated herein in their entirety.

This application is also generally related to U.S. patent application Ser. No. 12/209,631 (now U.S. Pat. No. 8,142,455), entitled Delivery of Minimally Invasive Lung Volume Reduction Devices; Ser. No. 12/209,662 (now U.S. Pat. No. 8,157,823), entitled Improved Lung Volume Reduction Devices, Methods and Systems, both of which were filed Sep. 12, 2008; and to Ser. No. 12/558,206, entitled Improved and/or Longer Lung Volume Reduction Devices, Methods, and Systems; and Ser. No. 12/558,197 (now U.S. Pat. No. 8,632,605), entitled Elongated Lung Volume Reduction Devices, Methods, and Systems, each of which were filed Sep. 11, 2009, all of which are incorporated herein by reference in their entirety.

All publications and patent applications mentioned in this specification are herein incorporated by reference to the same extent as if each individual publication or patent application was specifically and individually indicated to be incorporated by reference.

BACKGROUND OF THE INVENTION

Devices, systems and methods are described for treating lungs. The exemplary devices, systems and methods may, for example, improve the quality of life and restore lung function for patients suffering from emphysema. Embodiments of the systems may include an implant and a delivery catheter. The implant may be advanced through tortuous anatomy and actuated to retain a pre-determined shape and rigidity. Additionally, the implant may comprise a shape-memory material or spring material, which may be constrained to a first configuration during delivery through tortuous anatomy and then allowed to return to a second configuration during deployment. The deployed implant modifies the shape of the airways and locally compresses lung parenchyma to cause volume reduction and thereby tensions the lung parenchyma to restore elastic recoil. Systems and devices are also included that deploy and actuate the implantable devices, as well as systems and devices designed for recapture of the implanted device.

Current medical literature describes emphysema as a chronic (long-term) lung disease that can get worse over time. It's usually caused by smoking. Having emphysema means some of the air sacs in your lungs are damaged, making it hard to breathe. Some reports indicate that emphysema is the fourth largest cause of mortality in the U.S., affecting an estimated 16-30 million U.S. citizens. Each year approximately 100,000 sufferers die of the disease. Smoking has been identified as a major cause, but with ever increasing air pollution and other environmental factors that negatively affect pulmonary patients; the number of people affected by emphysema is on the rise.

A currently available solution for patients suffering from emphysema is a surgical procedure called Lung Volume Reduction (LVR) surgery whereby diseased lung is resected and the volume of the lung is reduced. This allows healthier lung tissue to expand into the volume previously occupied by the diseased tissue and allows the diaphragm to recover. High mortality and morbidity may be associated with this invasive procedure. Several minimally invasive investigational therapies exist that aim at improving the quality of life and restoring lung function for patients suffering from emphysema. These potential therapies include mechanical devices and biological treatments. The Zephyr™ device by Pulmonx (Redwood City Calif.) and the IBV™ device by Spiration (Redmond Wash.) are mechanical one way valve devices. The underlying theory behind these devices is to achieve absorptive atelectasis by preventing air from entering diseased portion of the lung, while allowing air and mucous to pass through the device out of the diseased regions.

The Watanabe spigot is another mechanical device that can seek to completely occlude the airway, thereby preventing air from entering and exiting the lung. Collateral ventilation (interlobar and intralobar—porous flow paths that prevent complete occlusion) may prevent atelectasis for such devices. The lack of atelectasis or lung volume reduction can drastically reduce the effectiveness of such devices. Other mechanical devices include means of deploying anchors into airways and physically deforming airways by drawing the anchors together via cables. Biological treatments utilize tissue engineering aimed at causing scarring at specific locations. Unfortunately, it can be difficult to control the scarring and to prevent uncontrolled proliferation of scarring.

Current minimally invasive treatments for chronic obstructive pulmonary disease such as valves, hydrogels, steam heat, or implants all provide treatments that are mechanically pre-determined and/or fixed or uncontrollable. In particular, such treatments often fail to account for the patient's current state or condition of tissue or disease progression, which may result in less than optimal treatment results. It would be desirable to provide improved medical devices, systems, and methods for the treatment of chronic obstructive pulmonary disease that overcome some of these challenges.

BRIEF SUMMARY OF THE INVENTION

The present invention generally provides improved medical devices, systems, and methods, particularly for treating one or both lungs of a patient with an implant. Specifically, implants of the present invention, such as coils, clips, or suitable mechanical devices, have a strength tuned or matched to a patient's particular tissue treatment region, taking into account the current state or condition of tissue and/or disease progression, for improved safety and efficacy clinical results. More particularly, embodiments of the present invention include a method for treating a lung of a patient with chronic obstructive pulmonary disease. The method comprises determining a regional tissue characteristic (e.g., density, strength, compliance) of at least a portion of lung tissue of the patient (e.g., at the treatment region) and selecting between first and second coils based on the determined regional tissue characteristic of the portion of lung tissue.

In particular, the first coil has a first austenite final tuning and second coil has a second austenite final tuning different than the first tuning. Determining may comprise imaging at least the portion of lung tissue of the patient so as to identify a localized lung tissue strength, density, or compliance of the tissue treatment region. For example, imaging modalities may comprise computed tomography (CT), magnetic resonance imaging (MRI), optical coherence tomography (OCT), ultrasound imaging, bronchoscope imaging, or fluoroscopy. Still further, stenography (e.g., shooting audible sound frequency through the trachea and measuring its sounds back as an indicator of tissue density or tension) or mechanical means (e.g., inflation catheters) may also be suitable for identifying localized lung tissue characteristics. After determining the regional tissue characteristic information, selecting may comprise matching the determined regional tissue density, strength, or compliance of the tissue treatment region to a strength of the first or second coil. The method further includes deploying the selected first or second coil in at least a portion of the lung so as to locally compress lung tissue.

The first and/or second coils may be formed from at least one alloy, such as nitinol, nickel, titanium, other shape-memory alloys, or a combination thereof (e.g., 50.8% nickel and 49.2% titanium). In the austenite phase, the metal coil recovers to its programmed shape. The temperature at which the metal coil has fully converted to an austenite phase is known as the austenite final temperature. The first austenite final tuning may be characterized by a first transition temperature of the alloy that is higher (or lower) than a second transition temperature of the second austenite final tuning. For example, the first transition temperature of the alloy may be just below a body temperature, such as a temperature in a range from about 30 degrees Celsius to about 35 degrees Celsius. The second transition temperature of the alloy may be in a range from about 5 degrees Celsius to about 15 degrees Celsius. In another example, the second transition temperature of the alloy may be in a range from about −26 degrees Celsius to about 10 or 15 degrees Celsius or in a range from about 15 degrees Celsius to about 30 degrees Celsius.

In some embodiments, determining comprises identifying a first region of lung tissue having a first regional tissue density, wherein selecting comprises selecting the first coil for deployment in the first region of the lung in response to the first regional tissue density. Further, a second region of the lung may be identified having a second regional tissue density different than the first regional tissue density, and the second coil may be selected for deployment in the second region of the lung in response to the second regional tissue density. The first coil has a first coil strength and the second coil has a second coil strength. The first coil strength may be less (or more) than the second coil strength. The determined regional tissue density indicates the first tissue region has a first tissue strength and the second tissue region has a second tissue strength, wherein the first tissue strength is less (or more) than the second tissue strength. In such an example, the second coil strength (which is stronger than the first coil strength) may be sufficiently mismatched to the first tissue strength (which is weaker than the second tissue strength) that deployment of the second coil in the first tissue region would be undesirable.

In additional embodiments, the first and second coils are included in a group of candidate coils having differing strengths at body temperature (e.g., high, medium, and low austenite final tuning for low strength to stronger coils) and lengths (e.g., 70-200 mm). A subset of the candidate coils may be selected for deployment in a first tissue region in response to a measurement of a length of the first tissue region, the subset of candidate coils having similar lengths and including the first coil and the second coil. Then the first, second or third coils (of similar lengths) of the smaller subset may be selected based on the determined regional tissue characteristic of the portion of lung tissue.

Selecting generally comprises matching a strength of the first or second coil to a current condition of the tissue treatment region, a state of disease progression, and/or the anatomical implantation location (e.g., differing geometric locations). For example, chronic obstructive pulmonary disease may comprises a disease progression such that the at least a portion of the lung tissue has a first lax tissue volume associated with the determined regional tissue density at a first time and an expected second lax tissue volume greater than the first lax tissue volume at a second time later than the first time. In this example, the selected first or second coil, when deployed in the at least a portion of the lung, is configured to compress the first lax tissue volume and to remain strained by the lung tissue at the first time, and is configured to also compress the second lax tissue volume at the second time.

After determining the regional tissue characteristic, selecting may comprise matching or tuning the determined regional tissue density or strength of the tissue treatment region to a strength of the first or second coil. For example, selecting may comprise matching a weaker portion of lung tissue with the first coil having a having a higher austenite final tuning than the second coil (e.g., low strength, weaker first coil) so as to provide a lower tensioning load on the weaker treatment tissue region. In particular, delivery of the selected first coil having a higher austenite final tuning into the lung of the patient may require less force to deploy the selected first coil than the (stronger) second coil. The selected first coil is also configured to apply a chronic constant force over a longer period of time than the second coil. Conversely, selecting may comprise matching a stronger portion of lung tissue with the second coil having a having a lower austenite final tuning than the first coil (e.g., stronger second coil) so as to provide a higher tensioning load on the stronger treatment tissue region.

In some embodiments, methods further comprise delivering the selected first or second coil into a lung of the patient, wherein the selected first or second coil is configured to compress a lung tissue volume. Still further, the selected first or second coil may be cooled below an austenite final temperature prior to or during delivery into the lung of a patient so as to convert the selected first or second coil temporarily to a martensitic metallic phase for easier coil delivery and deployment (or retrieval).

Embodiments of the present invention further include methods for treating a lung of a patient with chronic obstructive pulmonary disease by determining a first and second regional tissue characteristic (e.g., density, strength, compliance) of a first and second region of lung tissue of the patient, wherein the second tissue characteristic differs from the first tissue characteristic. A first implant having a first strength may be selected for deployment in the first region and in response to the first tissue characteristic. A second implant having second strength different than the first strength may be selected for deployment in the second region and in response to the second tissue characteristic. The first implant may be aligned or matched with the first tissue region for deployment therein so as to locally compress the lung tissue, while the second implant may be aligned or matched with the second tissue region for deployment therein so as to locally compress the lung tissue.

Embodiments of the present invention further include an implant assembly for treating a lung of a patient with chronic obstructive pulmonary disease. The implant may comprise an elongate body (e.g., coil, clip, or other mechanical device) having a constrained delivery configuration and a deployed bent configuration adapted to compress a lung tissue volume. The elongate body may comprise at least one alloy, wherein at least a portion of the elongate body (e.g., entire body, distal portion, proximal portion, intermediate portion) has a high austenite final tuning, wherein the high austenite final tuning is characterized by an austenite final temperature in a range from about 30 degrees Celsius to about 35 degrees Celsius.

The elongate body may have a high austenite final tuning that is characterized by a lower strength than an implant having a lower austenite final tuning when the elongate body is delivered to or deployed in lung tissue. Such an elongate body having high austenite final tuning is characterized by a lower tensioning load or force on the treatment tissue than an implant having a lower austenite final tuning. High austenite final implants advantageously allow for easier and more controlled implant delivery, deployment, and/or retrieval and as such accessibility to more airways of the lungs for potential treatment. In some instances, the implant assembly may further comprise a cooled loading cartridge or a cooled delivery catheter, as discussed in further detail below, containing the elongate body and configured to temporarily cool at least a portion of the elongate body below the austenite final temperature so as to temporarily convert the elongate body to a martensitic metallic phase.

Embodiments of the present invention further include methods for tuning a nitinol implant configured to treat a lung of a patient with chronic obstructive pulmonary disease. The method comprises heat treating the nitinol implant in a predetermined temperature range so that a strength of the implant is matched to a regional tissue characteristic (e.g., density, strength, or compliance) of at least a portion of lung tissue of the patient. The predetermined temperature range comprises about 505 Celsius to about 675 Celsius so as to lower an austenite final tuning and raise a strength of the metal implant. In other embodiments, the predetermined temperature range comprises about 325 Celsius to about 504 Celsius so as to increase an austenite final tuning and lower a strength of the metal implant. The heat treating processes to raise or lower the austenite final tuning are well understood by those of skill in the art. Generally, heat treating the nitinol implant comprises driving nickel into or out of a metal compound matrix so as to allow or smear a shape memory effect. The process generally involves placing the nitinol implant on a tool or carrier and putting this assembly in the oven under the temperatures described above so that the nitinol implant is sufficiently exposed to the heat. Generally, this heating process may be carried out in a time period in a range from 1 minute to about 5 minutes, so that the implant tooling is sufficiently heated. After removing the nitinol implant from the oven, it should be immediately quenched in cool fluid (e.g., water) to bring it back to ambient temperature.

Embodiments of the present invention further include methods for treating a lung of a patient with chronic obstructive pulmonary disease. Method include temporary tuning a metal implant configured to compress a lung tissue volume by lowering an austenite final temperature of the metal implant prior to or during delivery into the lung of a patient so as to convert the metal implant temporarily to a martensitic metallic phase. By temporarily tuning the metal implant, less force is required to deliver and/or deploy the metal implant in the desired treatment region within the lung, which in turn allows for easier implant delivery and/or deployment and accessibility to more airways of the lungs for potential treatment. Temporary tuning may be carried out in several ways. For example, at least a portion of the metal implant may be cooled so as to temporarily reduce a strength of the metal implant. Cooling in turn may comprises freezing the metal implant within an implant loading cartridge, inserting a cold fluid or gas (e.g., liquid nitrogen) around the metal implant or applying a suitable cooling element to the metal implant via an implant delivery catheter or device.

Embodiments of the present invention further include implant systems for treating a lung of a patient with chronic obstructive pulmonary disease. Such implant systems may include an elongate implant support having a proximal end and a distal end configured for advancement into the lung of a patient in alignment with a first region of a patient and a plurality of alternatively selectable implants. Each implant may comprise an elongate implant body deployable from an insertion configuration to a deployed configuration within the lung. The elongate body in the insertion configuration is advanceable distally within the lung by the implant support. The elongate body, when deployed from the insertion configuration to the deployed configuration in the lung, is configured to local compress an associated volume of lung tissue by applying an associated compressive load. The elongate bodies of the plurality of implants have differing strengths at body temperature and/or lengths so that the compressive loads are variably selectable by selecting and deploying a desired implant having a desired strength and length. The implant system may further include an imaging system suitable for identifying localized lung tissue strength or density.

Embodiments of the present invention further include an implant assembly for treating a lung of a patient with chronic obstructive pulmonary disease. The implant may comprise an elongate body having proximal and distal portions and an intermediate portion therebetween, wherein the elongate body has a constrained delivery configuration and a deployed bent configuration adapted to compress a lung tissue volume. At least two of the proximal, distal, and intermediate portions comprise at least one alloy having a first austenite final tuning (e.g., low austenite final) or a second austenite final tuning (e.g., high austenite final) different than the first austenite final tuning. For example, the intermediate portion may comprise the first austenite final tuning and the proximal and distal portions may comprise the second austenite final tuning. The low austenite final tuning results in the intermediate portion being characterized by a strength greater than the proximal and distal portions at body temperature. In another example, the intermediate portion may comprise the first austenite final tuning, the proximal portion may comprise the second austenite final tuning, and the distal portion may comprise a third austenite final tuning different than the first and second austenite final tunings.

Embodiments of the present invention further include methods for treating a lung of a patient with chronic or reversible obstructive pulmonary disease. The method includes determining a regional tissue compliance (e.g., lack of modulus or stiffness, looseness of tissue) of at least a portion of lung tissue of the patient and identifying a treatment location for deployment of a tissue compression implant as described herein in response to determining the tissue compliance. Determining tissue compliance may be evaluated in several ways. For example, evaluation may comprises measuring a displacement of the least portion of lung tissue during at least one cycle of inhalation and exhalation. Alternatively, determining may comprise video imaging the at least portion of the lung during at least one breathing cycle to qualitatively evaluate or grade tissue compliance. Still further, determining may comprise comparing at least two images of the at least portion of the lung, wherein the first image is taken during inhalation and the second image is taken during exhalation. The images may comprise a computed tomography (CT), magnetic resonance imaging (MRI), optical coherence tomography (OCT), ultrasound, bronchoscopic, or fluoroscopic images of at least the portion of lung tissue of the patient. Determining may still further comprise manipulating pressure changes in the lung with a balloon catheter device to determine tissue compliance as described in greater detail in U.S. Pat. No. 7,549,984 entitled Methods of Compressing a Portion of Lung, which is incorporated herein by reference in its entirety.

The method further includes deploying the implant at the identified treatment location so as to locally compress lung tissue. In particular, deploying may further comprise selecting between a first implant having a first austenite final tuning and second implant having a second austenite final tuning different than the first austenite final tuning. Generally, selecting comprises matching the determined regional tissue compliance of the portion of lung tissue to a strength of the first or second implant. For example, selecting may comprise matching a highly compliant tissue region (e.g., relatively significant displacement, separation, or movement of lung tissue during dynamic breathing) with the first implant having a lower austenite final tuning and characterized by a greater strength than the second implant at body temperature.

Alternatively, selecting may comprise matching a lower compliant tissue region with the second implant having a higher austenite final tuning and characterized by a lower strength than the second implant at body temperature.

The details of one or more implementations are set forth in the accompanying drawings and the description below. A better understanding of the features and advantages of the present invention will be obtained by reference to the description and drawings, and from the claims.

BRIEF DESCRIPTION OF THE DRAWINGS

FIGS. 12A-C schematically illustrate a lung having lower lobe tissue that is highly compliant and treatment of the lower lobe with a plurality of devices having stronger, low austenite final coils according to present invention.

DETAILED DESCRIPTION OF THE INVENTION

The present invention generally provides improved medical devices, systems, and methods for chronic obstructive pulmonary disease treatment, more particularly implant devices that are tuned as a function of the current state or condition of the treatment tissue (e.g., density, strength, compliance), disease progression, and/or implant location, for improved safety and efficacy clinical results. It will be appreciated that the lung is one of the largest organs in the body, where chronic obstructive pulmonary disease patients present with vastly different levels of enzymatic based destruction. This is an important observation because lung tissue can generally withstand a limited or fixed amount of stress, which is different depending on the condition of the treatment tissue and/or state of disease progression. Tissue destruction also presents itself in different geometric locations in the lung and treatments generally need to be placed where the lung is already not functioning. As such, it is important that any breathing mechanics that are sacrificed with the delivery and use of treatment devices do not further negatively affect the breathing capacity of the patient.

Figure 1A:
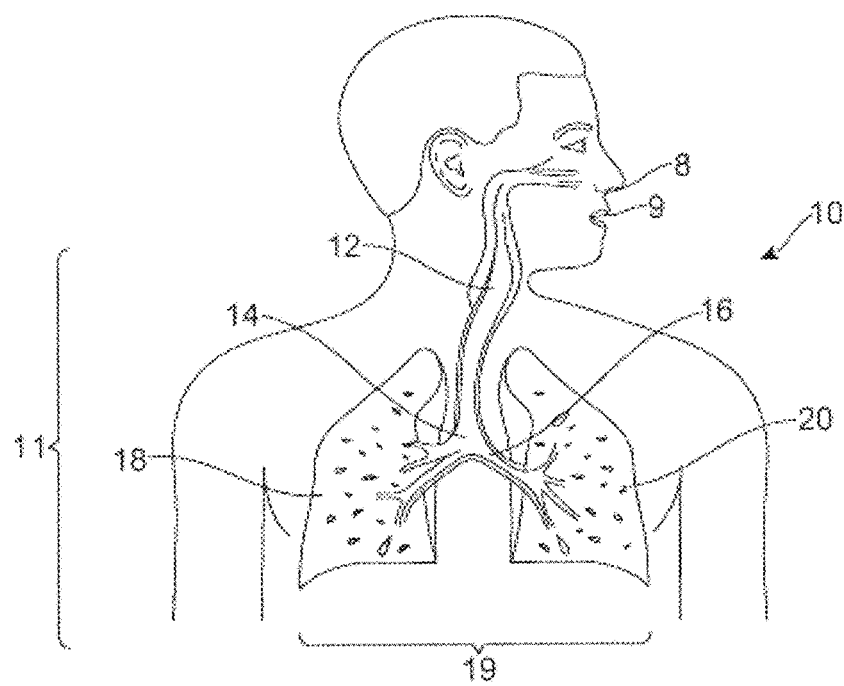
FIGS. 1A-C illustrate the anatomy of the respiratory system of a patient exhibiting varying tissue regions for treatment with lung volume reduction devices according to embodiments of the present invention.

By way of background and to provide context for the invention, FIG. 1A illustrates the respiratory system 10 located primarily within a thoracic cavity 11. This description of anatomy and physiology is provided in order to facilitate an understanding of the invention. Persons of skill in the art will appreciate that the scope and nature of the invention is not limited by the anatomy discussion provided. The respiratory system 10 includes the trachea 12, which brings air from the nose 8 or mouth 9 into the right primary bronchus 14 and the left primary bronchus 16. From the right primary bronchus 14 the air enters the right lung 18; from the left primary bronchus 16 the air enters the left lung 20. The right lung 18 and the left lung 20 together comprise the lungs 19. The left lung 20 is comprised of only two lobes while the right lung 18 is comprised of three lobes, in part to provide space for the heart typically located in the left side of the thoracic cavity 11, also referred to as the chest cavity.

Figure 1B:
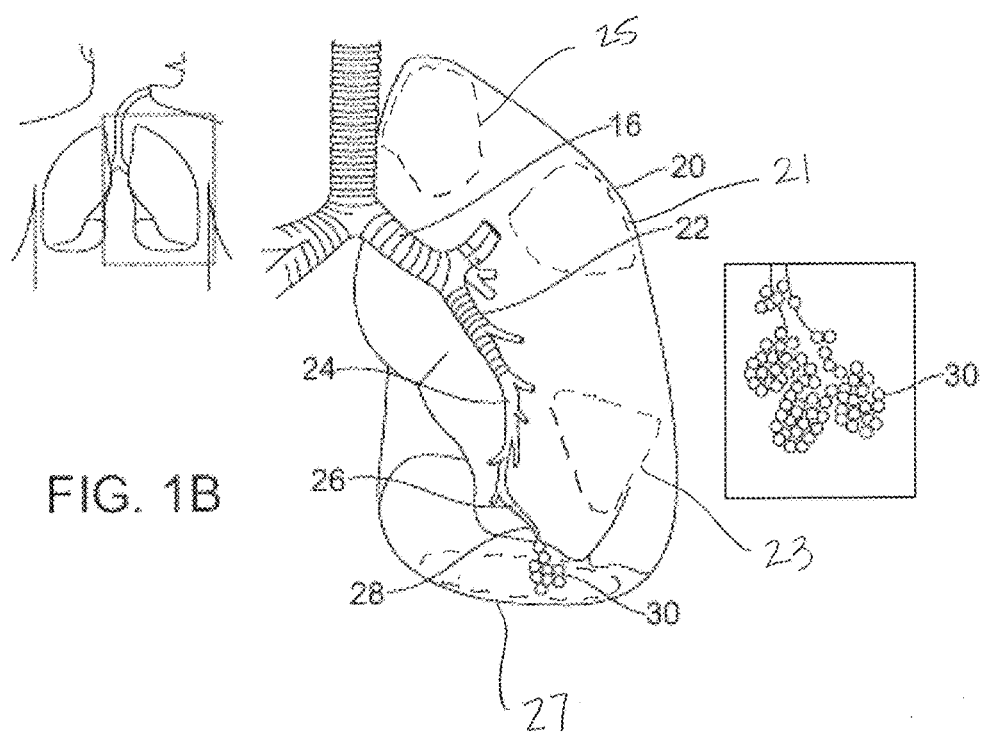
Figure 1C:
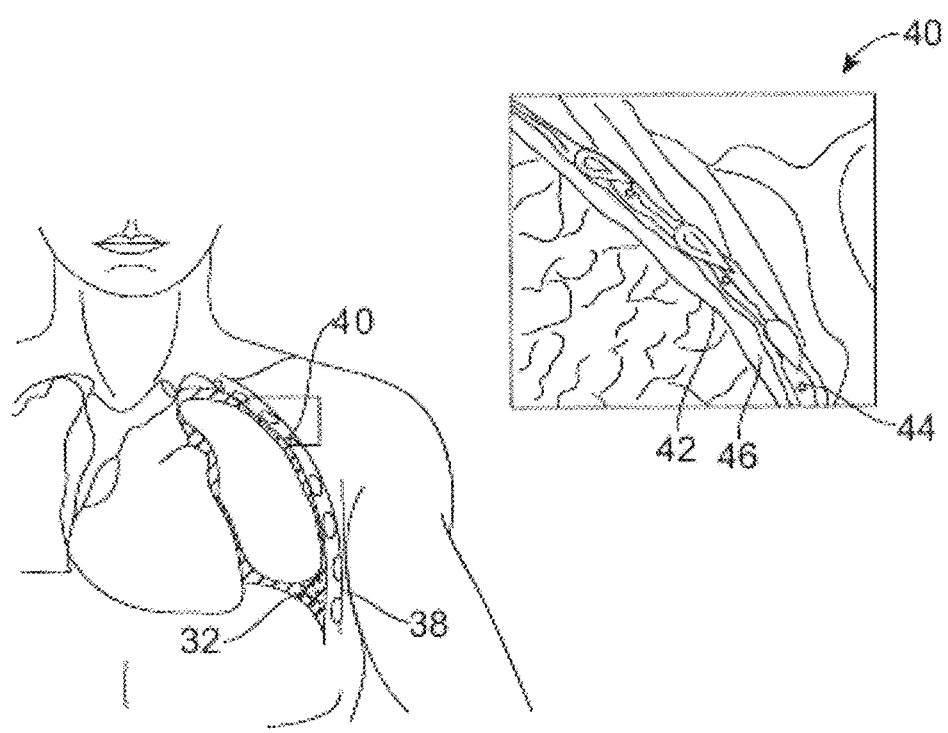

As shown in more detail in FIG. 1B, the primary bronchus, e.g. left primary bronchus 16, that leads into the lung, e.g. left lung 20, branches into secondary bronchus 22, and then further into tertiary bronchus 24, and still further into bronchioles 26, the terminal bronchiole 28 and finally the alveoli 30. The pleural cavity 38 is the space between the lungs and the chest wall. The pleural cavity 38, shown in FIG. 1C, protects the lungs 19 and allows the lungs to move during breathing. Also shown in FIG. 1C, the pleura 40 defines the pleural cavity 38 and consists of two layers, the visceral pleurae 42 and the parietal pleurae 44, with a thin layer of pleural fluid therebetween. The space occupied by the pleural fluid is referred to as the pleural space 46. Each of the two pleurae layers 42, 44, are comprised of very porous mesenchymal serous membranes through which small amounts of interstitial fluid transude continually into the pleural space 46. The total amount of fluid in the pleural space 46 is typically slight. Under normal conditions, excess fluid is typically pumped out of the pleural space 46 by the lymphatic vessels.

The lungs 19 are described in current literature as an elastic structure that floats within the thoracic cavity 11. The thin layer of pleural fluid that surrounds the lungs 19 lubricates the movement of the lungs within the thoracic cavity 11. Suction of excess fluid from the pleural space 46 into the lymphatic channels maintains a slight suction between the visceral pleural surface of the lung pleura 42 and the parietal pleural surface of the thoracic cavity 44. This slight suction creates a negative pressure that keeps the lungs 19 inflated and floating within the thoracic cavity 11. Without the negative pressure, the lungs 19 collapse like a balloon and expel air through the trachea 12. Thus, the natural process of breathing out is almost entirely passive because of the elastic recoil of the lungs 19 and chest cage structures. As a result of this physiological arrangement, when the pleura 42, 44 is breached, the negative pressure that keeps the lungs 19 in a suspended condition disappears and the lungs 19 collapse from the elastic recoil effect.

When fully expanded, the lungs 19 completely fill the pleural cavity 38 and the parietal pleurae 44 and visceral pleurae 42 come into contact. During the process of expansion and contraction with the inhaling and exhaling of air, the lungs 19 slide back and forth within the pleural cavity 38. The movement within the pleural cavity 38 is facilitated by the thin layer of mucoid fluid that lies in the pleural space 46 between the parietal pleurae 44 and visceral pleurae 42. As discussed above, when the air sacs in the lungs are damaged 32, such as is the case with emphysema, it is hard to breathe. Similarly, locally compressing regions of the lung tissue while maintaining an overall volume of the lung increases tension in other portions of the lung tissue, which can increase the overall lung function.

FIG. 1B illustrates the anatomy of the respiratory system of a patient exhibiting varying tissue regions 21, 23 presenting differing tissue characteristics for treatment. As discussed above, it will be appreciated there can be variations in tissue and anatomical characteristics of an individual, as a result of a variety of factors. Emphysema patients generally present with loose tissue that fails to recoil in an elastic way which in turn fails to radially support the airways to hold them open during exhalation. The methods, devices, and systems of the present invention seek to provide improved treatments for effective and safe restoration of the recoil effect. For example, a tissue treatment region 21 characterized by loose tissue that has significant enzymatic destruction may be weak and even moderate loads imposed by a lung volume reduction device may tear, puncture, or otherwise damage or distort the tissue. As such, it would be desirable to provide treatments (e.g., high austenite final coil) in these lower tissue density locations that provide a low force to restore radial outward support. As discussed with reference to FIGS. 10A and 10B, this is of particular advantage in chronic situations so as to provide sustained support that will not overwhelm the weak tissue yet continue to compress lung tissue during disease progression. Other tissue treatment regions 23 may be characterized by very dense loose tissue of greater strength and as such this tissue may be fully capable of taking a treatment (e.g., low austenite final coil) that provides a high tensioning load to restore radial outward support. Still further, other factors such as tissue compliance, treatment locations (upper lobe treatment regions 25 vs. lower lobe treatment regions 27), anatomical characteristics, state of disease (e.g., homogeneous or heterogeneous emphysema), and/or state of disease progression may also influence selection of lung volume reduction treatment devices of a desired strength.

Figure 2:
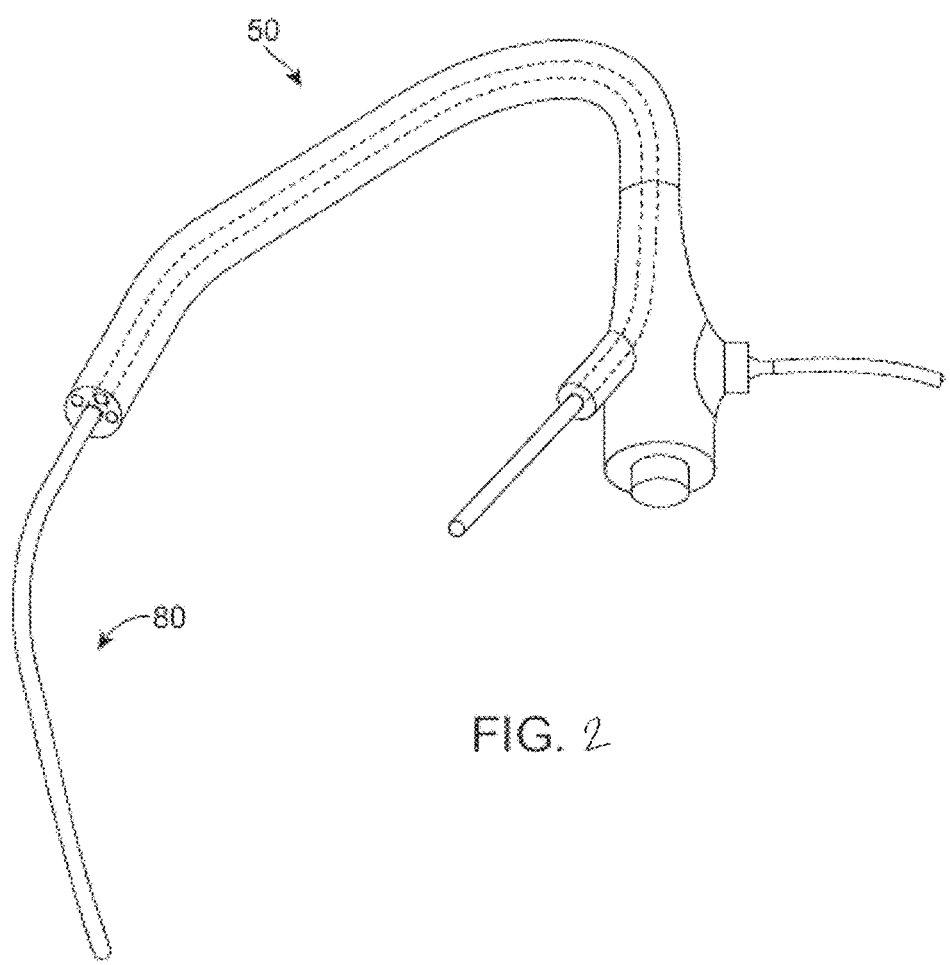
FIG. 2 illustrates a bronchoscope in combination with a delivery device for a lung volume reduction device according to embodiments of the present invention.

FIG. 2 illustrates the use of a lung volume reduction delivery device 80 for delivering a lung volume reduction device comprising an implantable device with the bronchoscope 50. The lung volume reduction system, as described in further detail below, is adapted and configured to be delivered to a lung airway of a patient in a delivery configuration and then transitioned to a deployed configuration. By deploying the tuned device (e.g., of desired strength), appropriate tension can be applied to the surrounding treatment tissue which can facilitate effective and safe restoration of the elastic recoil of the lung.

Figure 3A:
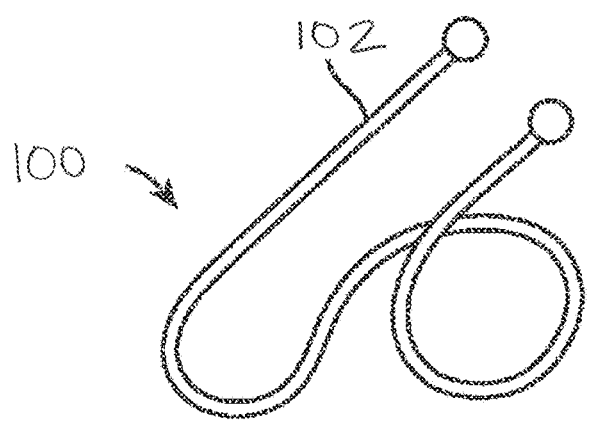
FIGS. 3A-C illustrate various lung volume reduction devices according to embodiments of the present invention.

The device is generally designed to be used by an interventionalist or surgeon. FIG. 3A illustrates an implant device 100 that is shaped in a three dimensional shape similar to the seam of a baseball. The wire is shaped so that proximal end 102 extends somewhat straight and slightly longer than the other end. This proximal end will be the end closest to the user and the straight section will make recapture easier. If it were bent, it may be driven into the tissue making it difficult to access. The devices generally comprise a shape-memory material, however a person of ordinary skill would recognize that many of the methods described herein may be used to configure a tuned device (e.g., of desired strength) such that it may be mechanically actuated and locked into a similar configuration.

Figure 3B:
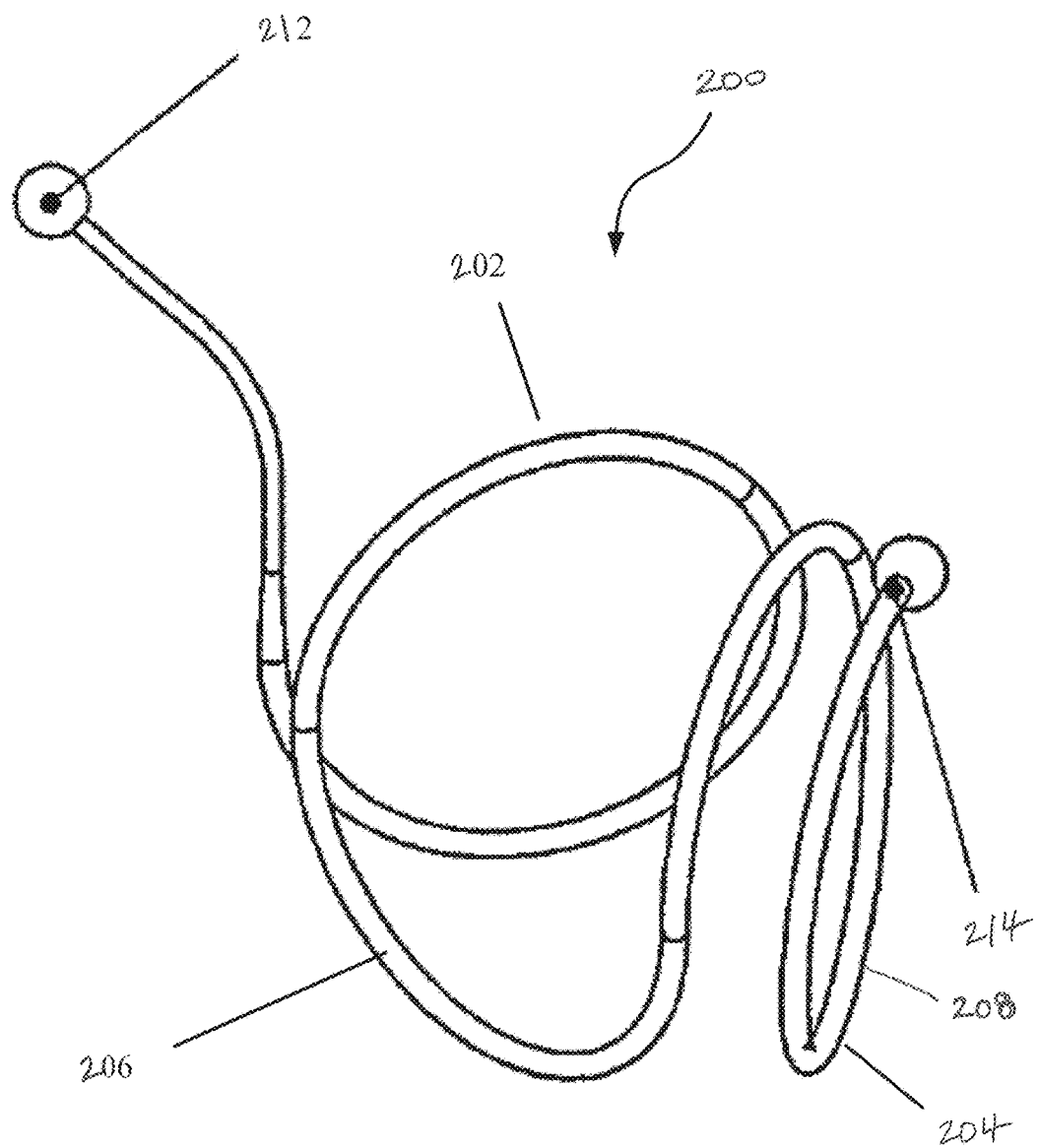

FIG. 3B illustrates another implant device 200 in a pre-implantation or a post-implantation configuration. In this configuration, device 200 includes two helical sections 202, 204 with a transition/intermediate section 206 disposed between the two helical sections 202, 204. Similar to the devices described herein, device 200 may have another configuration which corresponds to a delivery configuration in which the device assumes during delivery to a treatment region within an airway. Each helical section 202, 204 includes a respective helical axis 206, 208. In the embodiment shown, helical axis 206 is at an angle with helical axis 208. The angle between the helical axis 206 and helical axis 208 may be between 190° and 230° in some embodiments. In alternative embodiments, helical section 202, 204 may share a helical axis. The proximal end 212 and distal end 214 comprise atraumatic balls.

In this particular embodiment, device 200 includes a right-handed helical section and a left-handed helical section and the transition section between the two helical sections comprises a switchback transition section when the device is in the pre-implantation or post-implantation configuration. The switchback transition section may be defined as the intermediate section where the elongate body of the implant transitions between oppositely handed helical configurations. In some embodiments, the switchback transition section may reduce the recoil forces during device 200 deployment thereby providing greater control of device 200 during deployment. Additionally, the switchback transition may reduce migration of the implant after deployment and thus maintain the device's tissue compression advantages. As shown, the helical sections do not have to include the same number of loops or complete helix turns. In this embodiment the distal helix 204 comprises more loops than the proximal helix 202.

Alternatively, device 200 may be configured such that the proximal helix 202 includes more loops than distal helix 206. The helical sections may be configured to include a pitch gap of 0.078±0.025 in. In this particular embodiment, the two helical sections are circular helical sections. Other embodiments of the present invention may be configured to include spherical or conical helical sections when in a pre-implantation or post-implantation configuration.

Figure 3C:
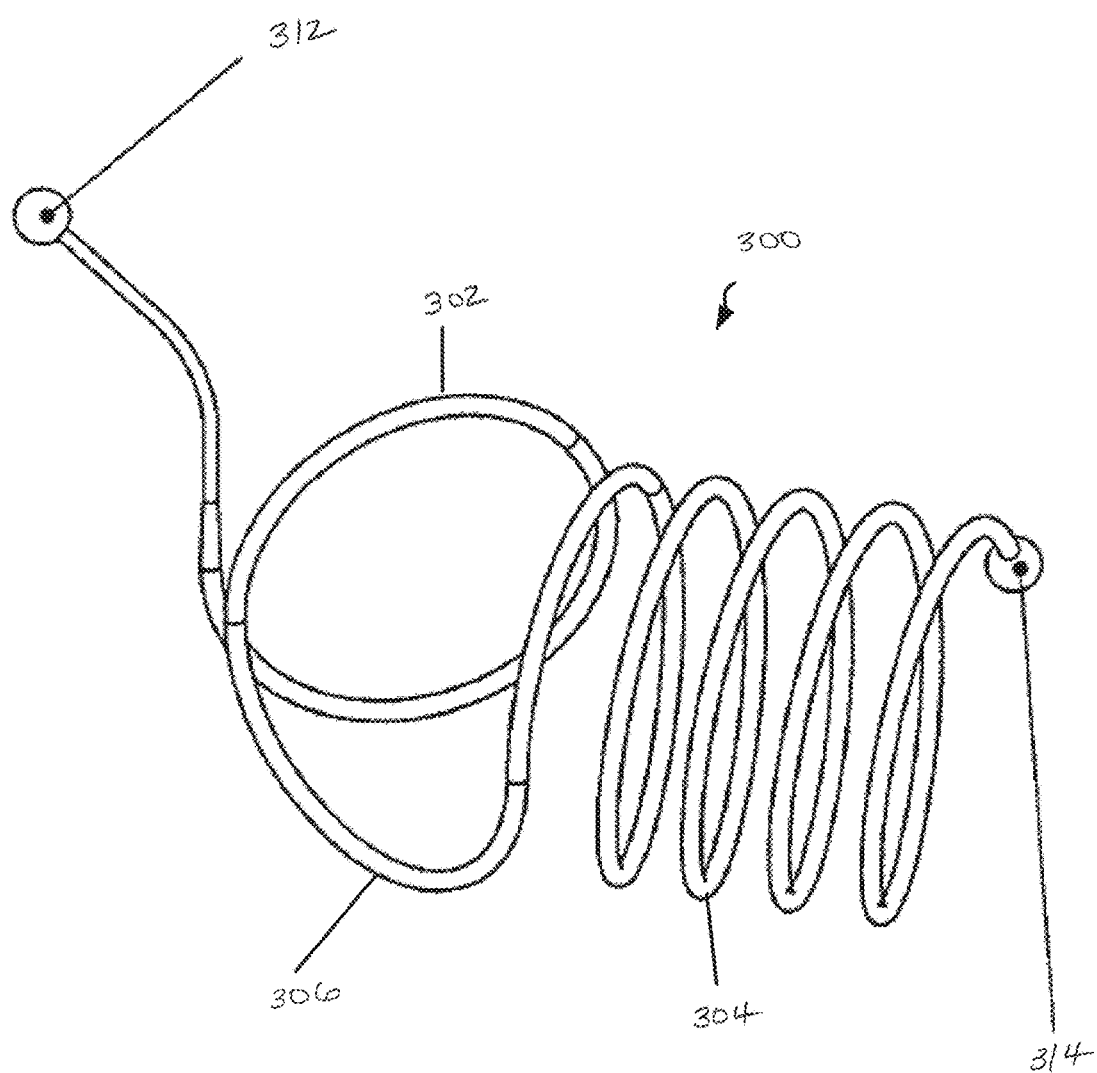

FIG. 3C illustrates device 300 which is similar to device 200. Device 300 includes a proximal helical section 302 and a distal helical section 304. A transition 306 is disposed between the two helical sections 302, 304. The proximal end 312 and distal end 314 comprise atraumatic balls. As shown, the distal helical section 304 includes 4.25 loops but may comprise more. The devices of FIGS. 3A-C are adapted and configured to be delivered to a lung airway of a patient in a delivery configuration and to change to a deployed configuration to bend the lung airway. The devices are characterized in that the devices have a delivery configuration that is resiliently bendable into a plurality of shapes, such as the ones depicted herein. The design of the devices can be such that strain relief is facilitated on both ends of the device. Further the ends of the device in either the delivery or deployed state are more resilient.

In operation the devices shown in FIGS. 3A-C are adapted and configured to be minimally invasive which facilitates easy use with a bronchoscope procedure. Typically, there is no incision and no violation of the pleural space of the lung during deployment. Furthermore, collateral ventilation in the lung does not affect the effectiveness of the implanted device. As a result, the devices are suitable for use with both homogeneous and heterogeneous emphysema. Embodiments of the lung volume reduction system can be adapted to provide an implant that is constrained in a first configuration to a relatively straighter delivery configuration and allowed to recover in situ to a second configuration that is less straight configuration. Devices and implants can be made, at least partially, of spring material that will fully recover after having been strained at least 1%. As described herein, suitable material includes a metal, such as metals comprising nickel and titanium. Each of the devices depicted in FIGS. 3A-C are adapted and configured to impart bending force on lung tissue. For example, a spring element can be provided that imparts bending force on lung tissue. The implantable spring element that can be constrained into a shape that can be delivered to a lung airway and unconstrained to allow the element to impart bending force on the airway to cause the airway to be bent.

Lung volume reduction systems, such as those depicted in FIGS. 3A-C, comprise an implantable device that is configured to be deliverable into a patient's lung and which is also configured to be reshaped to make the lung tissue that is in contact with the device more curved. Increasing the curvature of the tissue assists in reducing the lung volume of diseased tissue, which in turn increases the lung volume of healthier tissue. In some instances, the devices are configured to be reshaped to a permanent second configuration. However, as will be appreciated by those skilled in the art, the devices can also be adapted and configured to have a first shape and is configured to be strained elastically to a deliverable shape.

As will be appreciated by those skilled in the art, the devices illustrated in FIGS. 3A-C can be configured to be deliverable into a patient's lung and configured to reshape lung tissue while allowing fluid to flow both directions past the implant. A number of additional features described in related U.S. patent application Ser. No. 12/558,206 entitled Enhanced Efficacy Lung Volume Reduction Devices, Methods, and Systems, such as lock features, decoupler systems, activation systems, and retrieval systems may be used with aspects of the present invention. The full disclosure of U.S. patent application Ser. No. 12/558,206 is incorporated herein by reference.

Figure 4:
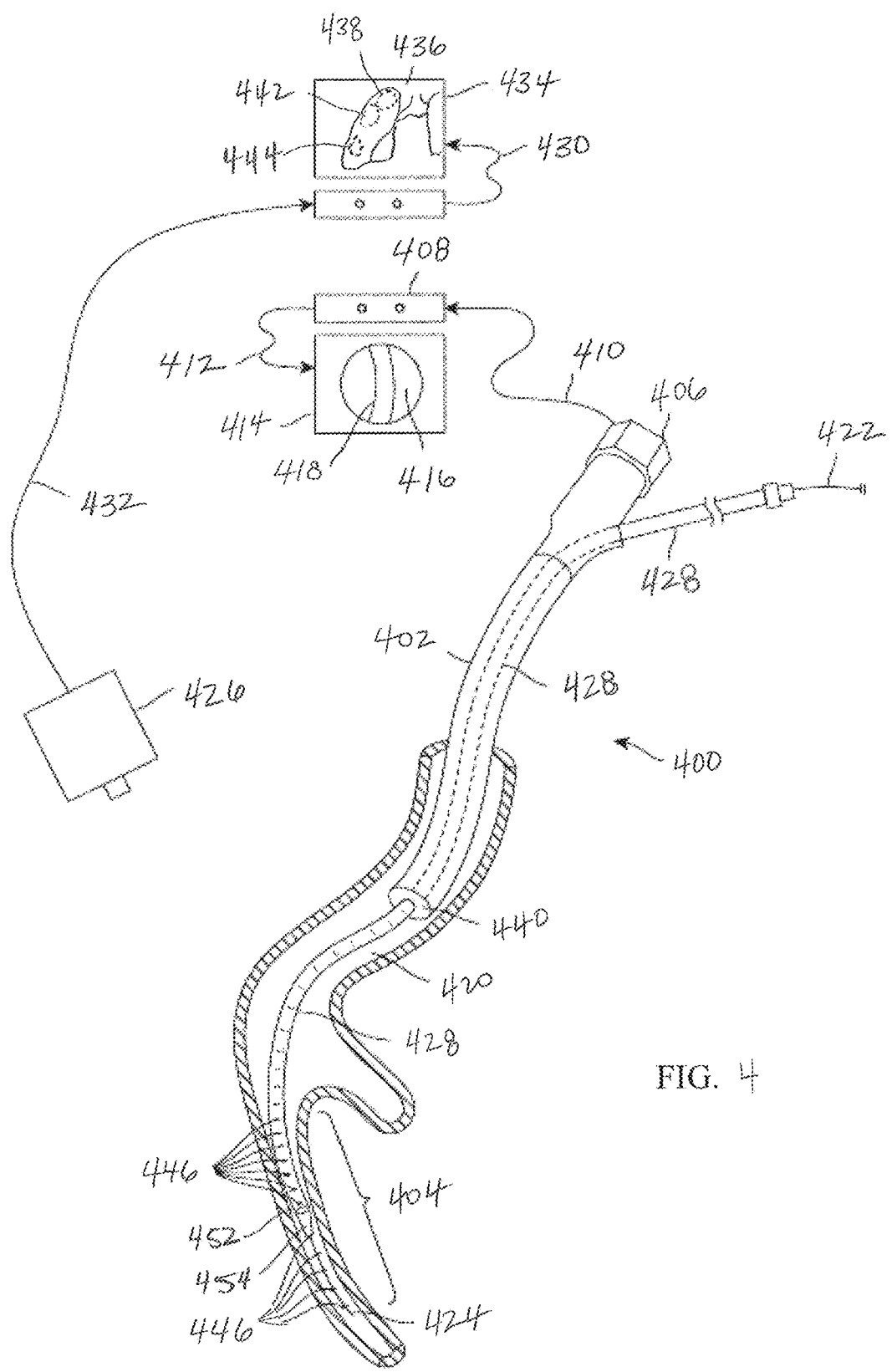
FIG. 4 illustrates a lung volume reduction implant system including a bronchoscope, imaging system, delivery catheter, dilator, and guidewire according to embodiments of the present invention.

FIG. 4 illustrates delivery system 400 as placed into a patient body, and particularly into a human lung. The distal end 440 of bronchoscope 402 extends into an airway system toward an airway portion or axial region 404, sometimes referred to as an axial segment. The scope camera 406 is coupled to a video processor 408 via a cable 410. The image is processed and sent through a cable 412 to a monitor 414. Monitor 414 shows on screen 416 a portion of a delivery catheter image 418 just ahead of the optical image capture element in the scope. In some embodiments, the scope may be constrained by a relatively large cross-section to advancement only to a "near" region of the lung adjacent the major airways. Hence, the optical image has a viewfield that extends only a limited distance along the airway system, and it will often be desirable to implant some, most, or all of the implant beyond a field of view 420 of scope 402.

Guidewire 422 is threaded through bronchoscope 402 and through the airway system to (and through) airway 404. As described above, guidewire 422 may optionally have a cross-section significantly smaller than that of the scope and/or the delivery catheter. Alternative embodiments may use a relatively large diameter guidewire. For example, rather than relying on a tapering dilator between the guidewire and the delivery catheter, the guidewire may instead be large enough to mostly or substantially fill the lumen of the delivery catheter, while still allowing sliding motion of the guidewire through the lumen. Suitable guidewires may have cross-section in a range from about 5 Fr to about 7 Fr, ideally being about 5½ Fr, while the delivery catheter may be between about 5 Fr and 9 Fr, ideally being about 7 Fr. A distal end 424 of the guidewire 422 may be angled as described above to facilitate steering. Still further variations are also possible, including delivery of the implant directly thru a working lumen of an endoscope (with use of a separate delivery catheter). In particular, where a cross-sectional size of a bronchoscope allows the scope to be advanced to a distal end of the target airway region, the bronchoscope itself may then be used as a delivery catheter, optionally without remote imaging.

A fluoroscopic system, an ultrasound imaging system, an MRI system, a CT system, OCT system, bronchoscope optical system, or some other remote imaging modality having a remote image capture device 426 allows guidance of the guidewire so that the guidewire and/or delivery catheter 428 can be advanced beyond the viewing field of bronchoscope 402. In some embodiments, the guidewire may be advanced under remote image guidance without the use of a scope. Regardless, the guidewire can generally be advanced well beyond the near lung, with the distal end of the guidewire often being advanced to and/or through the mid-lung, optionally toward or to the small airways of the far lung. When a relatively large guidewire is used (typically being over 5 Fr., such as a 5½ Fr guidewire), the cross-section of the guidewire may limit advancement to a region of the airway having a lumen size appropriate for receiving the implants described above. The guidewire may have an atraumatic end, with exemplary embodiments having a guidewire structure which includes a corewire affixed to a surrounding coil with a resilient or low-column strength bumper extending from the coil, the bumper ideally formed by additional loops of the coil with separation between adjacent loops so as to allow the bumper to flex axially and inhibit tissue damage. A rounded surface or ball at the distal end of the bumper also inhibits tissue injury. A distal end 452 of laterally flexible delivery catheter 428 can then be advanced through the lumen within bronchoscope 402 and over guidewire 422 under guidance of the imaging system, ideally till the distal end of the delivery catheter is substantially aligned with the distal end of the guidewire 424.

Remote imaging modality 426 is coupled to imaging processor 430 via cable 432. Imaging processor 430 is coupled to a monitor 434 which displays an image 436 on the screen. As discussed herein, methods, devices, and system of the present invention advantageously utilize the information from a patient's image file 426 with analysis to determine regional tissue characteristics (e.g., density and/or strength) of a treatment region 438, 442, 444 and use that information to tune the intrinsic strength (e.g., high, medium, and low austenite final tuning for low strength to stronger coils) of the implant device 100 so that the strength of the device 100 is sufficiently matched to the tissue characteristic(s) of the lung tissue region being treated.

Figure 5:
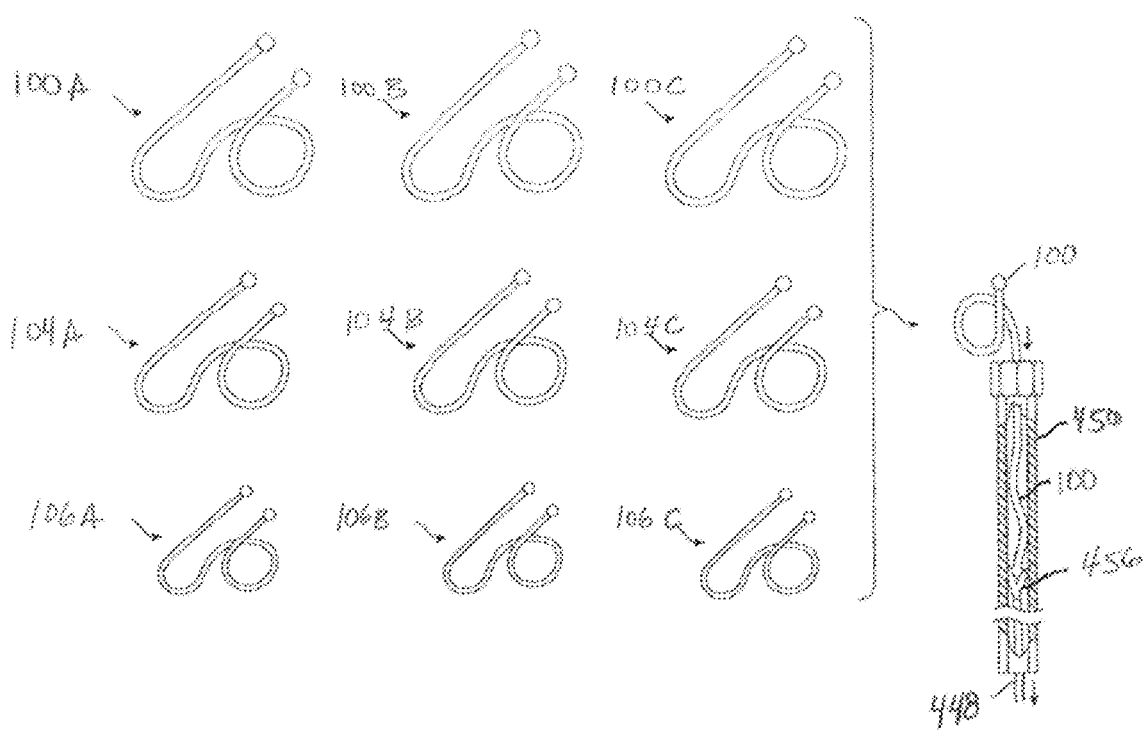
FIG. 5 schematically illustrates selection from among a plurality of alternative devices with different strengths at body temperature and lengths and loading of a selected device into a cooled cartridge so that the device can be advanced into the delivery catheter of FIG. 4.

FIG. 5 shows a plurality of alternatively selectable implants including implants 100A-C, 104A-C, and 106A-C. These implants may have elongate bodies having different strengths (e.g., low strength to stronger coils) at body temperature and/or different lengths (or sizes, shapes, etc.) from each other. In particular, implants 100A-C, 104A-C, and 106A-C may comprise larger to smaller length coils respectively, while implants 100A, 104A, and 106A may comprise a high austenite final coil, implants 100B, 104B, and 106B may comprise an intermediate austenite final coil, and implants 100C, 104C, and 106C may comprise a low austenite final coil. The elongate body when deployed is configured to locally compress an associated volume of lung tissue by applying an associated compressive load. The implants have differing strengths at body temperature or in the body so that the compressive loads are variable selectable by selecting and deploying a desired implant having a desired strength. As such, the selected implant is programmed to deliver specific amounts of force to the treatment region of the lung when deployed.

As discussed earlier, permanent tuning of nitinol implants may be accomplished by means of tuning the locations of nickel in the alloy which adjusts the austenite final transition temperature of the metal so that the pseudo-elastic plateau is adjusted up or down depending on the amount of strength that is desired. Tuning the austenite final temperature up lowers the strength (e.g., weaker coil) at body temperature, while tuning the austenite final temperature down raises the strength (e.g., stronger coil) at body temperature. Austenite final tuning of nitinol may be accomplished by heat treating the metal at or nearly at 505 degrees Celsius. This drives nickel into or out of the metal compound matrix of the material which has the effect of allowing or smearing the shape memory effect of nitinol. Short heat treatments (e.g., long enough to elevate the entire metallic part to temperature) above 505 degrees Celsius lowers the austenite final. For example, the temperature range may be from about 505 to 675 degrees Celsius depending on how much the austenite final needs to be tuned. Heat treatments below 505 degrees Celsius (e.g., 325-504 degrees Celsius) raises the austenite final.

With higher austenite final, the alloy delivers less strength. With a lower austenite final, the alloy will deliver more strength. With the ability to tune the metal up or down or both, a process can be utilized that will get the implant to a permanent state where the austenite final is tuned to the patient's tissue characteristics. Tuning austenite final to zero or below will yield a device that performs similar with the properties of common super or pseudo elastic nitinol alloys. Adjusting the austenite final temperature higher will lower the loading and unloading plateau. If the implant austenite final temperature is tuned as high as body temperature, the device will not recover to a programmed shape in the body and the chronic forces on the tissue will be zero. The implant may be tuned anywhere in the range from below zero to body temperature, depending on the patient's treatment tissue.

Referring to FIG. 4, in the case of a patient with weak tissue region 438, implants 100A, 104A, and/or 106A may be desired for implantation as they have an austenite final tuned near but just below body temperature to reduce the strength to almost zero and yet provide chronic force that will be constantly applied and an effect that will be seen for a longer period of time than if the force was higher. This is because the lung is large and visco-elastic strain occurs when a strong implant is delivered that distorts the tissue if the density is not high enough to withstand the force. If the tissue is really compromised due to disease progression (e.g., voids of tissue, significant tissue damage/destruction, floppy/floating tissue), deployment of a strong implant could potentially rupture or tear the treatment tissue. High austenite final coils may also provide improved chronic results as such low strength coils provide sustained support that will not overwhelm the weak tissue yet continue to compress lung tissue during elongation of the tissue over time. Likewise, a high tissue density region 444 (e.g., little or no voids) may be treated with stronger coils 100C, 104C, and/or 106C and intermediate tissue density region 442 may be treated with lower strength coils 100B, 104B, and/or 106B for more acute verifiable results.

When using delivery system 400, guidewire 422 may be advanced to a target region near the distal end of the airway system. Guidewire 422 may be advanced distally until further distal advancement is limited by the distal end of the guidewire being sufficiently engaged by the surrounding lumen of the airway system. Delivery catheter 428 can then be advanced so that a distal end of catheter 428 is adjacent a distal end of the guidewire 424. The distance along the indicia of length from the bronchoscope 402 to the distal end of guidewire 424 may be used to select an implant having an elongate body 100, 104, or 106 with a desired length. The desired length may be lesser, greater or about the same as the distance between the distal end of delivery catheter 428 (or guidewire 424) and the distal end of the bronchoscope as indicated by the indicia 446.

The indicia 446 may comprise scale numbers or simple scale markings, and distal end 452 of catheter 428 may have one or more corresponding high contrast indicia, with the indicia of the guidewire 422 and the indicia of the catheter 428 typically visible using the remote imaging system, such as x-ray or fluoroscopy. Hence, remote imaging camera 426 can also identify, track or image indicia 446 and thus provide the length of the guidewire portion extending between (and the relative position of) the distal end of the bronchoscope and the distal end of guidewire 424. Indicia of length 446 may, for example, comprise radiopaque or sonographic markers and the remote imaging modality as described above may comprise, for example, an x-ray or fluoroscopic guidance system, a computed tomography (CT) system, an MRI system, or the like. Exemplary indicia comprise markers in the form of bands of high-contrast metal crimped at regular axial intervals to the corewire with the coil disposed over the bands, the metal typically comprising gold, platinum, tantalum, iridium, tungsten, and/or the like. Note that some of the indicia of the guidewire are schematically shown through the distal portion of the catheter in FIG. 4. Indicia of length 446 thus facilitate using a guidance system to measure a length of airway 404 or other portion of the airway system beyond the field of view of the scope, thereby allowing an implant of appropriate length to be selected.

As further shown in FIG. 4, when a small-diameter guidewire is used, a dilator 454 may be advanced through the lumen of the catheter so that the distal end of the dilator extends from the distal end of delivery catheter 452 when the catheter is being advanced. Dilator 454 atraumatically expands openings of the airway system as delivery catheter 428 advances distally. Dilator 454 tapers radially outwardly proximal of the distal tip of guidewire 424, facilitating advancement of the catheter distally to or through the mid-lung toward the far lung. Once the catheter has been advanced to the distal end of airway portion 404 targeted for delivery (optionally being advanced over the guidewire to the distal end of the guidewire when a large diameter guidewire is used to identify a distal end of a target region for an implant, or as far as the cross-section of the catheter allows the catheter to be safely extended over a smaller diameter guidewire), the length of the airway (optionally between the distal end of the guidewire and the distal end of the bronchoscope) is measured. The dilator 454 (if used) and guidewire 422 are typically withdrawn proximally from deliver catheter 428 so as to provide an open lumen of the delivery catheter from which a lung volume reduction device or implant can be deployed.

Exemplary implants may be more than 10% longer than the measured target airway axial region length, typically being from 10% to about 300% longer, and ideally being about 100% longer. Suitable implants may, for example, have total arc lengths of 50, 75, 100, 125, 150, 175, and 200 mm. The devices can have any suitable length for treating target tissue. However, the length typically range from, for example, 2 cm to 20 cm, usually 12.5 cm. The diameter of the device can range from 1.00 mm to 3.0 mm, preferably 2.4 mm. The device is used with a catheter which has a working length of 60 cm to 200 cm, preferably 90 cm.

Related U.S. patent application Ser. No. 12/558,206 describes exemplary methods for treating a patient and evaluating the treatment, each of which may be used with aspects of the present invention. For example, the treatment method may comprise delivering an implant within the lung and then evaluating the patient's breathing thereafter to determine whether more implants and/or what types of implants (e.g., varying strength, length, etc.) are needed. Alternatively, a plurality of implants may be delivered within the patient's lungs before an evaluation. The patient's lungs may be evaluated by measuring a forced expiratory volume (FEV) of the patient, measuring/visualizing displacement of the diaphragm or of the lung fissures, and like parameters to determine whether more implants and/or what types of implants (e.g., varying strength, length, etc.) are needed.

As shown in FIG. 5, the elongate body 100 having the selected strength and length may be advanced and deployed into the lung via the airway system and using pusher grasper 448. In particular, the selected implant 100 may be loaded into a loading cartridge 450 (and subsequently into the lumen of delivery catheter 428) using pusher grasper device 448. Pusher grasper device 448 may be tensioned proximally and/or loading cartridge 450 may be pushed distally so that elongate body 100 straightens axially. The loading cartridge 450 and implant 100 can then be coupled to the other components of the delivery system, and the implant advanced into the airway as described below in FIG. 6.

In exemplary embodiments, the pusher grasper 448 moves distally while the catheter 428 is retracted proximally from over the implant during deployment. The selected implant may have a length greater than the measured distance between the distal end of the guidewire (and hence the end of the delivery catheter) and the distal end of the scope. This can help accommodate recoil or movement of the ends of the implant toward each during delivery so as to avoid imposing excessive axial loads between the implant and tissue. Distal movement of the pusher grasper 448 and proximal end of the implant 100 during deployment also helps keep the proximal end of the implant within the field of view of the bronchoscope, and enhances the volume of tissue compressed by the implant.

To provide a desirable implant shelf life and/or a desirable deployment force for compressing tissues using self-deploying elongate bodies (including those using resilient materials and/or using superelastic materials such as nitinol or the like), it may be advantageous to store and/or deliver the various implants of various strengths at body temperature and sizes in a relaxed state. For example, the implant loading cartridge 450 may cool implant 100 below body temperature in the delivered configuration. In such an embodiment, the cooling system can be controlled by a temperature sensing feedback loop and a feedback signal can be provided by a temperature transducer in the system. The implant 100 can be configured to have an austenite final temperature adjusted to 37 degrees Celsius or colder. Additionally, at least a portion of the metal of the device 100 can be transformed to the martensite phase in the delivery configuration so as to make the device flexible and very easy to deliver.

In particular, by temporarily tuning the metal implant to adjust the strength of the implant down, less force is required to deliver and/or deploy the metal implant in the desired treatment region within the lung. This in turn allows for easier and more controlled implant delivery and/or deployment and accessibility to more airways of the lungs for potential treatment. Temporary tuning may be carried out by applying temporary cooling so that the device is cooled below the austenite start transition temperature. Tuning the austenite final up to nearly body temperature such as 30-35 degree Celsius (e.g., just below 37 degrees Celsius body temperature) also allows the device to be temporarily cooled below the austenite final temperature to fully convert the metal to a martensite metallic phase condition during deployment. The metal implant may behave like a soft metal with nearly no elastic range so it can be bent very easily as it is navigated through the brochoscope and into the lung. As described above, dropping the temperature of the implant during delivery can be alternatively achieved by freezing it (e.g., freezing it in a thin tube full of saline so it is pushed out and surrounded by ice to keep it cooled), by use of a cooling element (e.g., peltier cooling array), and/or by purging cold fluid or gas past the implant while it is in the delivery catheter.

Figure 6:
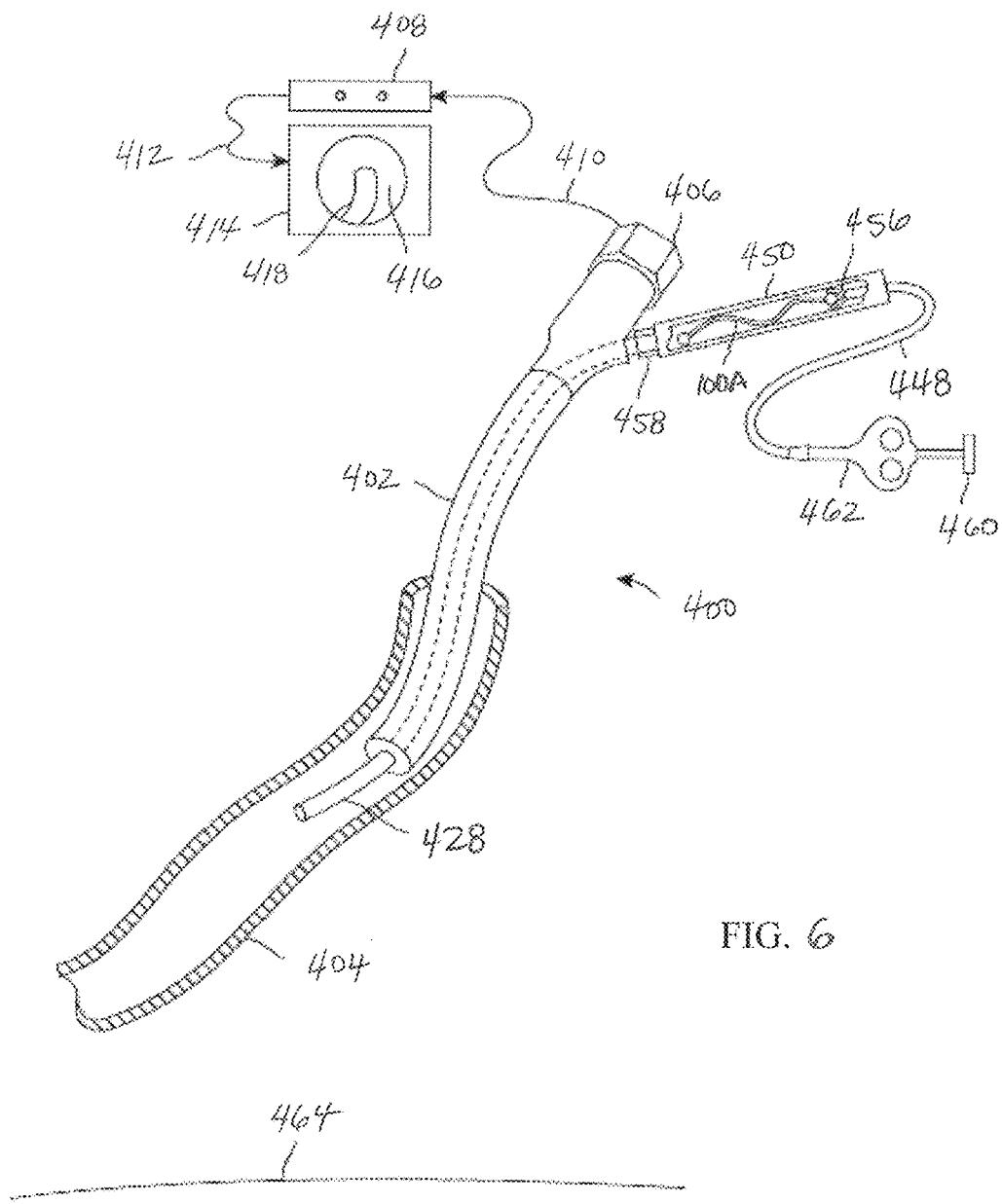
FIG. 6 illustrates a lung volume reduction implant system in an airway of a lung illustrating delivery of a lung volume reduction device according to embodiments of the present invention.

FIG. 6 illustrates the delivery system 400 that has been placed into a human lung after the desired implant 100 having the selected strength and/or length has been chosen, as described above with reference to FIGS. 4 and 5. The bronchoscope 402 is in an airway 404. The scope camera 406 is coupled to a video processor 408 via a cable 410. The image is processed and sent through a cable 412 to a monitor 414. The monitor shows a typical visual orientation on the screen 416 of a delivery catheter image 418 just ahead of the optical element in the scope. The distal end of the delivery catheter 428 protrudes out of the scope in an airway 404 where the user will place the selected implant device, for example coil 100A. The implant 100A is loaded into a loading cartridge 450 that is coupled to the proximal end of the delivery catheter via locking hub connection 458. A pusher grasper device 448 is coupled to the proximal end of the implant 100A with a grasper coupler 456 that is locked to the implant using an actuation plunger 460, handle 462 and pull wire that runs through the central lumen in the pusher catheter. By releasably coupling the pusher to the selected implant device 100A and advancing pusher/grasper device 448, the user may advance the implant to a position in the lung in a deployed configuration. The user can survey the implant placement position and still be able to retrieve the implant back into the delivery catheter, with ease, if the delivery position is less than ideal. The device has not been delivered and the bottom surface of the lung 464 is shown as generally flat and the airway is shown as generally straight. These may both be anatomically correct for a lung with no implant devices. If the delivery position is correct, the user may actuate the plunger 460 to release the implant 100A into the patient.

It will be appreciated that delivery of a mechanical device, such as coils, is difficult in that it needs to be delivered into the body in a generally straightened configuration as discussed herein. Mechanical devices of the present invention take advantage of the properties of superelastic nitinol. The elastic range is large with this material so that the metal springs back to a pre-programed shape after the delivery catheter constraints have been removed. However, the implant device is always trying to spring back throughout the entire delivery process and this often creates friction that makes the delivery difficult. Advantageously, higher austenite final coils, such as implant 100A, are more malleable and as such are more easily deployable (e.g., minimize push/pull) as less forces are required during delivery into the lung. Higher austenite final implants generally enable more controlled implant delivery and as such this allows for several benefits, such as greater access to more airways of the lungs for potential treatment, other device design configurations, etc.

Figure 7:
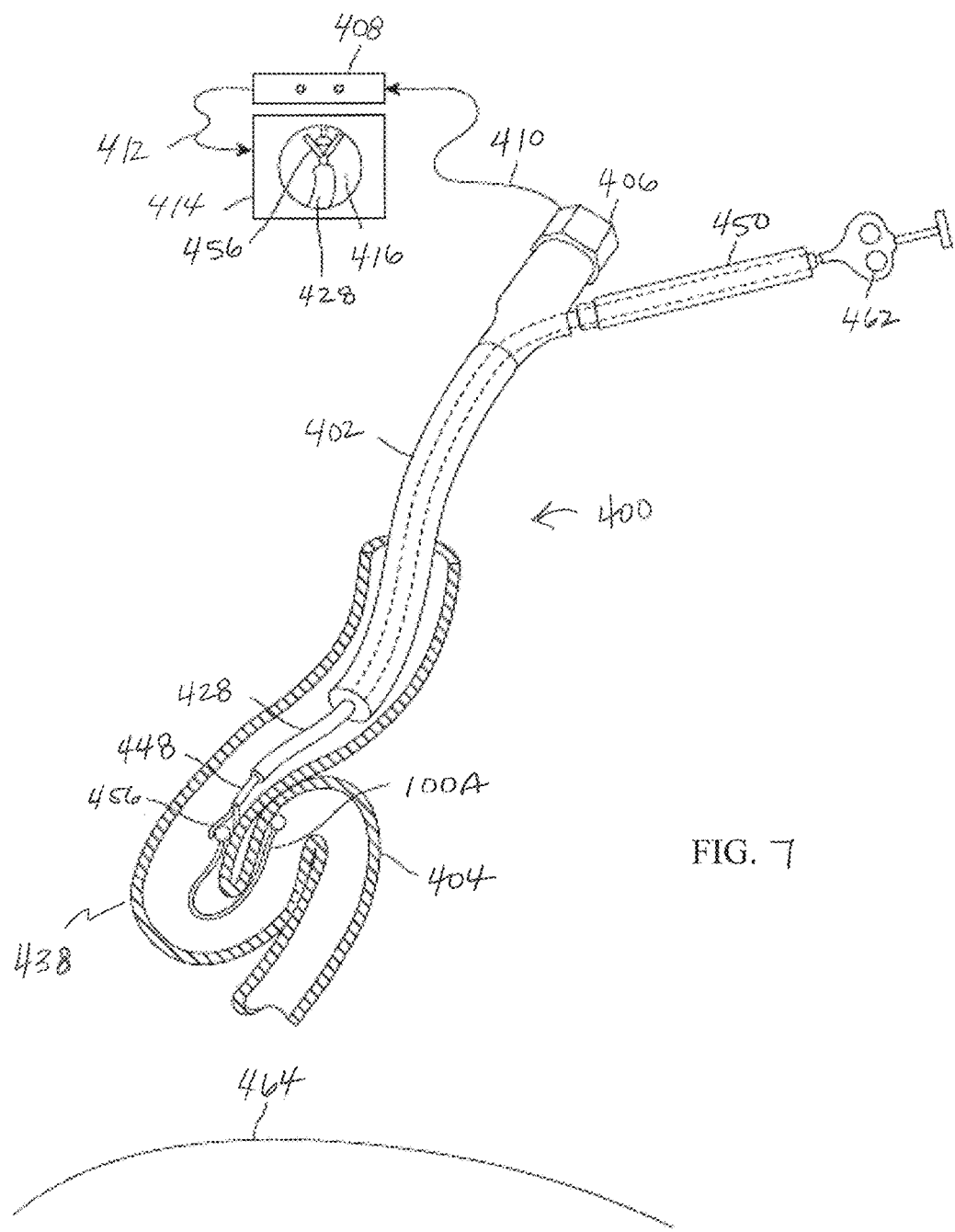
FIG. 7 illustrates a lung volume reduction implant system in an airway of a lung illustrating deployment of a lung volume reduction device according to embodiments of the present invention.

FIG. 7 illustrates generally the same system after the selected implant 100A has been deployed into the airway 404. By deploying the flexible, higher austenite final coil 100A, sufficient tension can still be applied to the surrounding low density treatment tissue 438 (as less force is needed to fold this tissue), while facilitating safer restoration (e.g., no puncturing or tearing of tissue by implant) of the elastic recoil of the lung. In particular, the implant 100A and pusher 448 has been advanced through the delivery catheter 428 to a location distal to the scope 402. The pusher grasping jaws 456 are still locked onto the proximal end of the implant 100A but the implant has recovered to a pre-programmed shape that has also sufficiently bent the airway 404 into a folded configuration. By folding the airway, the airway structure has been effectively shortened within the lung and lung tissue between portions of the implant has been laterally compressed. Since the airways are well anchored into the lung tissue, the airway provides tension on the surrounding lung tissue which is graphically depicted by showing the pulled (curved inward) floor of the lung 464. The image from the camera is transmitted through the signal processor 408 to the monitor 414 to show the distal tip of the delivery catheter 428, distal grasper of the pusher 456, and proximal end of the implant 100A. The grasper 456 may be used to locate, couple to and retrieve devices that have been released in the patient. The implant performs work on the airways and lung tissue without blocking the entire lumen of the airway. This is a benefit in that fluid or air may pass either way through the airway past the implant device 100A.

In some embodiments, an implant is deployed in a straight configuration with the use of a catheter, e.g., catheter 428, to contain it in a generally straight shape. Alternative embodiments may use the working lumen of the bronchoscope directly so that the bronchoscope is used as a delivery catheter. Upon removal of the constraining catheter, the implant recoils to a deployed shape that can be easily identified by the fact that the distance from one end to the second is reduced. The proximal end of the implant may be grasped, e.g., with pusher grasper device 456, and held so that the distal end of the implant remains engaged against the desired airway tissue as the length of the implant is progressively unsheathed (by withdrawing the catheter proximally). High tensile forces might be generated between the distal portion of the implant and the airway tissue if the proximal end of the implant is held at a fixed location throughout deployment, as the implant is biased to recoil or bring the ends together when released. Hence, it can be advantageous to allow the proximal end of the implant to advance distally during release, rather than holding the implant from recoiling, as these forces may be deleterious. For example, the distance and tissue thickness between the distal end of the implant and the lung surface is short, there may be little strain relief on the tissue and the risk of rupture may be excessive. Additionally, the implant might otherwise tend to foreshortened after it is released by the grasper. When foreshortening occurs, the proximal end of the implant may travel distally beyond the viewing field of the bronchoscope and the user can have difficulty retrieving the implant reliably.

Figure 8A:
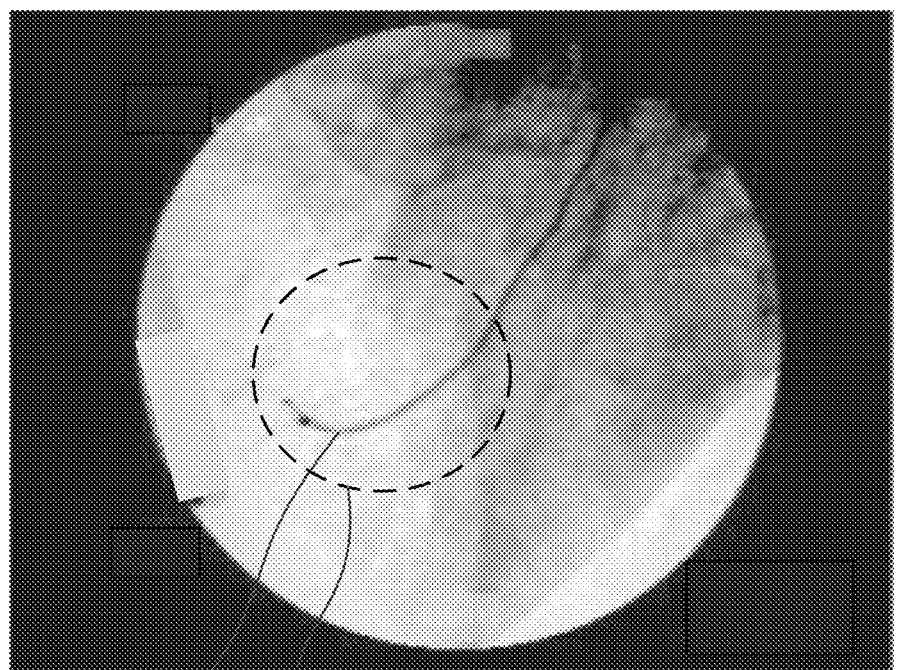
FIGS. 8A-B illustrate images of human lung tissue before and after a tissue treatment region is compressed by an embodiment of an implant having a desired strength matched or tuned to the identified tissue treatment characteristic according to the present invention.
Figure 8B:
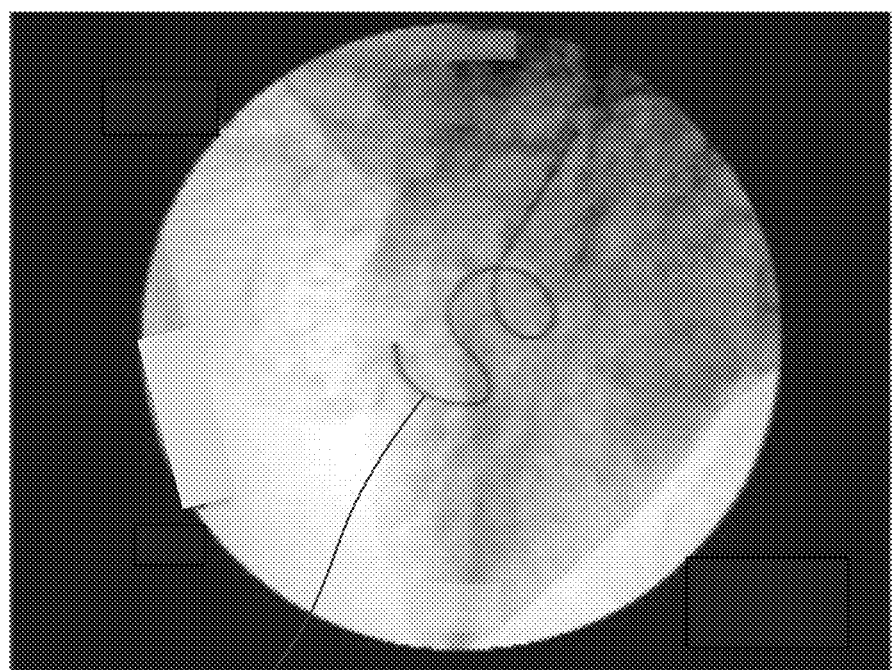

FIGS. 8A and 8B illustrate two images of a human lung in a chest cavity simulator. The lungs were explanted from a person who expired due to chronic obstructive pulmonary disease (COPD). The cavity is sealed with the lung's main stem bronchi protruding through a hole in the cavity wall. The bronchi has been sealed to the hole so a vacuum can be applied to aspirate the air from the space between the cavity interior and the lung. This allows the lung to be drawn to a larger expanded condition with vacuum levels that are physiologic (such as 0.1 to 0.3 psi, similar to that of the typical human chest cavity). FIG. 8A illustrates a 175 mm long implant that has been delivered to a distal end of a delivery catheter 428 as described above. The catheter is substantially constraining the implant in a straightened delivery configuration. This image further illustrates a treatment region 438 characterized by voids of tissue indicative of weak tissue having a low regional tissue density or strength. As such, implant 100A may be desired for implantation as it has an austenite final tuned near but just below body temperature to reduce its strength and yet provide chronic force that will be constantly applied and an effect that will be seen for a longer period of time than if the force was higher.

FIG. 8B shows the implant after the catheter 428 has been retracted from the implant 100A to allow the implant to return toward its relaxed configuration. The implant has recovered to its original shape by means of elastic recoil. The delivery grasper has been unlocked to release the implant in the airway. By comparing the lung tissue in FIGS. 8A and 8B, the regions of the lung that are compressed by the implant during the process of shape recovery (changing from a delivered shape to a deployed shape) can be identified. The compressed regions are visualized in the fluoroscopic images by distinct increases in darkness or darker grey shades of the images. Darker regions identify more dense regions (FIG. 8B) and lighter identify less dense regions (FIG. 8A). The implant can be seen to compress regions as it recovers to cause areas of the lung to become darker. As can be seen, the airway lining may be pinched thereby providing beneficial tissue compression. In some embodiments, a 70% improvement in volume reduction over current LVRC can be obtained.

The implants of the present invention can be placed in pathologic regions in the lung that provide limited or no exchange of gas to and from the blood stream because the alveolar walls used to do so have been degraded and destroyed by disease. These are typically the most degraded regions that have lost mechanical strength and elasticity. In an inhaling COPD patient these degraded areas fill with air first, at the expense of gas filling in regions that could better help the patient, because the weakened tissue presents little to no resistance to gas filling. By implanting the selected devices (based on strength, length, etc.) in these areas, resistance is provided so the gas is filled in regions that still can effectively exchange elements to and from the blood stream. Viable regions have structure remaining so resistance to gas filling is present as this is a normal physiologic property. The implant advantageously provides more gas filling resistance in the destroyed regions than the normal physiologic resistance in the viable regions so gas flows to viable tissue. This eliminates or reduces the counterproductive "preferential filling" phenomenon of the most diseased lung tissue prior to treatment. The implantable device may also delay collapse of airways during a breathing cycle thereby limiting the amount of air trapping in a lung. Accordingly, patients with small airway disease or with alpha 1-antitrypsin deficiency may also be treated with such a device. Additionally, the implantable device may be configured to provide enhanced breathing efficacy immediately after implantation while still allowing gas exchange distal to the deployed implant thereby reducing the chance of atelectasis of lung tissue distal to the implant.

Figure 9:
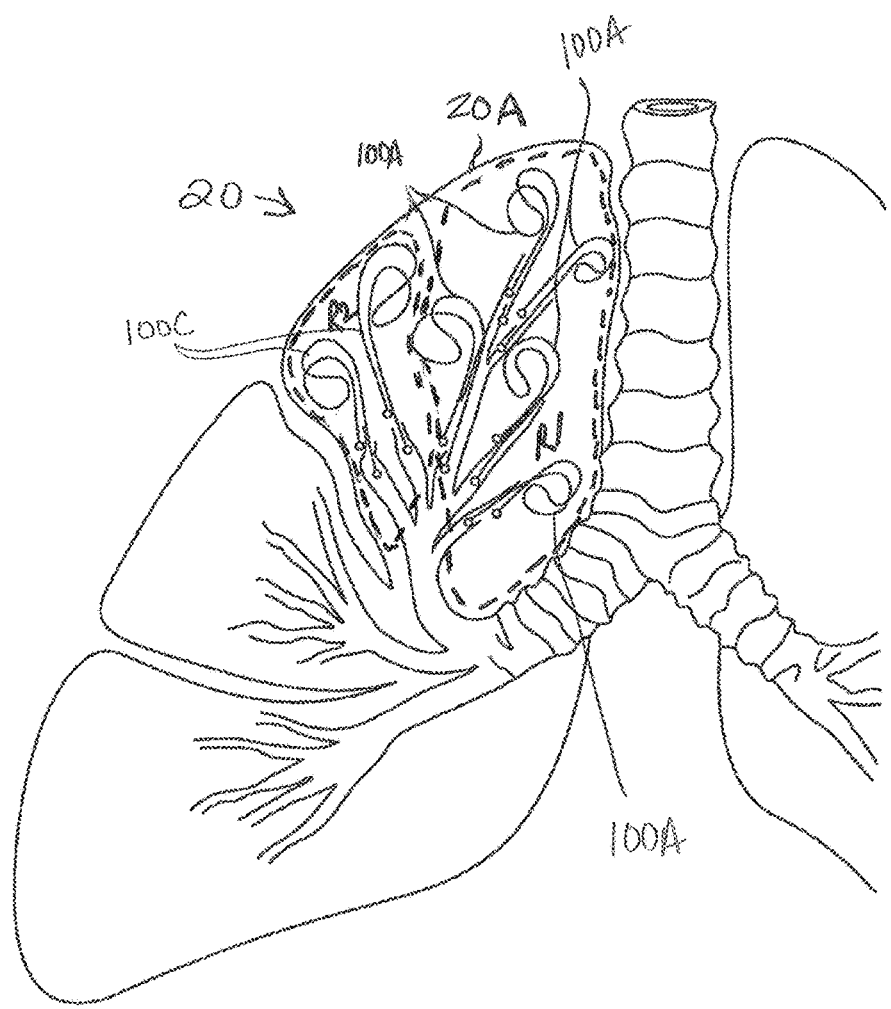
FIG. 9 schematically illustrates a lung that has an upper lobe with tissue treatment regions having varying characteristics that are treated by a plurality of devices having varying austenite final strengths that are suitably tuned to the respective treatment regions according to present invention.

FIG. 9 is a schematic illustration of a lung 20 that has an upper lobe 20A having two regions defined by vastly different regional tissue characteristics denoted by R1 and R2. For example, the first tissue region R1 may be weak due to disease progression so that deployment of lower strength implants 100A may be desired to facilitate effective and safe folding of the lung tissue in region R1. Likewise, the high tissue density region R2 may be effectively treated with stronger implants 100C as more force may be required to fold the lung tissue in region R2. A lobe will often have between 2 and 20 devices deployed therein, optionally having between 3 and 15 devices, and in some cased between 5 and 10 devices (7 devices are shown deployed in FIG. 9). The devices have recovered to or near their relaxed shape and the ends of the devices include locally enlarged cross-sections in the form of rounded balls, as described above, so as to help the ends of the device remain in the airways they were delivered into.

Figure 10A:
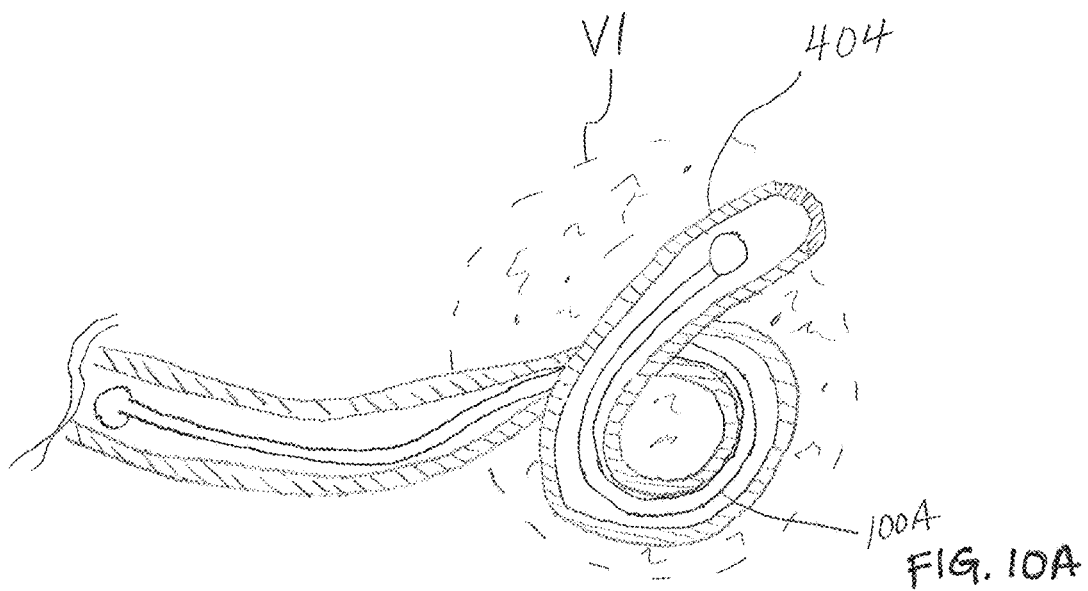
FIGS. 10A-B schematically illustrate a lung undergoing disease progression over a period of time and the ability of the implant device to continually compress the variable tissue volume over time according to the present invention.
Figure 10B:
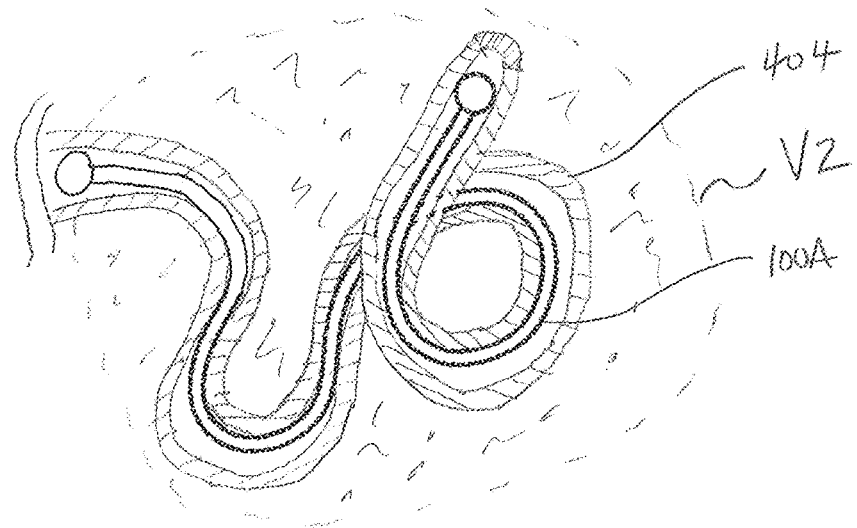

FIGS. 10A-B schematically illustrate a lung undergoing disease progression over a period of time (e.g., months to years) and the ability of the implant device 100A deployed within the airway 404 to continually compress the variable tissue volume over time as the disease progresses. As discussed above, chronic obstructive pulmonary disease may comprises a disease progression such that the lung tissue has a first lax tissue volume V1 associated with the determined regional tissue density (e.g., low density tissue) at a first time as shown in FIG. 10A and an expected second lax tissue volume V2 greater than the first lax tissue volume V1 at a second time (e.g., one year later) as shown in FIG. 10B. In this example, the selected coil 100A, when deployed is configured to compress the first lax tissue volume V1 and to remain strained by the lung tissue at the first time (FIG. 10A), and is configured to also compress the second lax tissue volume V2 at the second time (FIG. 10B).

Figure 11A:
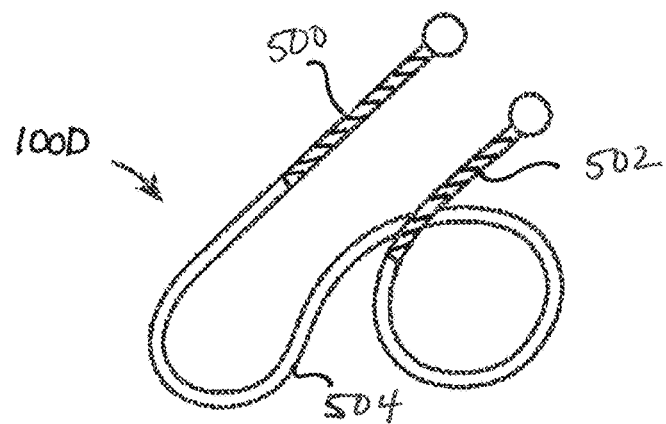
FIGS. 11A-C illustrate still further lung volume reduction devices according to embodiments of the present invention.
Figure 11B:
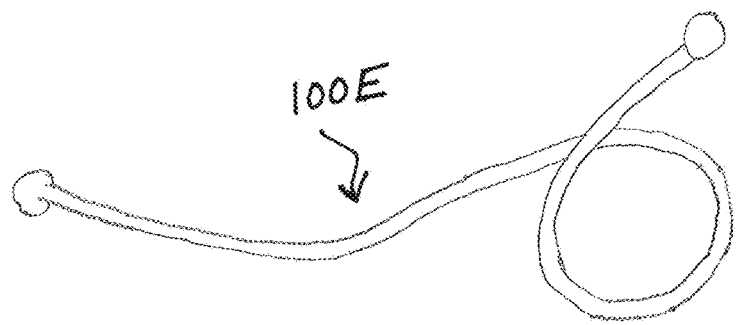
Figure 11C:
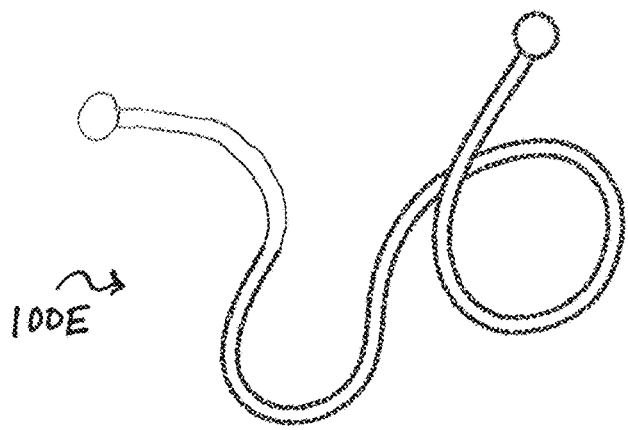

FIGS. 11A-C illustrate still further lung volume reduction coils according to embodiments of the present invention. FIG. 11A illustrates an implant coil 100D having a proximal portion 500, a distal portion 502, and an intermediate portion 504 between proximal and distal portions 500, 502. In particular, the different portions of the coil 100D may be selectively treated (e.g., resistively heated) so as to provide a single implant having different austenite final tuned regions along a length thereof. In some instances, lung volume reduction devices experience the greatest flexure or moment in the intermediate or middle portion thereof. By providing multiple points of flexure (via different austenite final tuned portions along a length of the coil), the strain over the entire length of the coil may be reduced or lowered which in turn improves fatigue resistance of the implanted coil over time. In this particular example, the intermediate portion 504 may comprises a low austenite final tuning while the distal and proximal portions 500, 502 may comprise a high austenite final tuning so that the coil is strongest in the middle and weaker at the ends. The coil 100D is shown to have greater fatigue resistance over time than coils 100E of FIGS. 11B and 11C, which have the same austenite final tuning along an entire length thereof.

Referring now to FIGS. 12A and 12B, a left lung 20 is schematically illustrated showing an upper lobe 20A and a lower lobe 20B. FIG. 12A illustrates an image of the lung during inhalation or inspiration where the diaphragm contracts and pulls the lungs downward and FIG. 12B illustrates the lung during exhalation or expiration where the diaphragm relaxes and the lungs move upwards. The compliance (e.g., lack of modulus or stiffness, looseness of tissue) of the lung tissue may be evaluated in several ways as discussed above. In this example, the first image of the lungs during inhalation in FIG. 12A may be compared to the image of the lungs during exhalation in FIG. 12B to illustrate that the lower lobe tissue 20B is highly compliant based on the substantial separation of the lung lobes 20A, 20B during breathing. In some patient populations, it may be of benefit to determine a physiologic tissue compliance of at least a portion of lung tissue of the patient so as to identify an appropriate treatment location for deployment of a tissue compression implant. For example, patients who do not suffer from significant tissue destruction but still suffer from air trapping within the lungs and have difficulty breathing can still benefit from the lung volume reduction devices of the present invention. Such patients may generally be characterized as suffering from chronic or reversible obstructive pulmonary disease. Typically, evaluating such patients for treatment based solely on tissue characteristics such as density may be inadequate as such patients morphology may not necessarily present itself as the typical emphysema patient.

The methods of the present invention advantageously involve evaluating tissue compliance as an alternative or in addition to determining a tissue density of a lung tissue so as to identify an appropriate treatment location for deployment of a lung volume reduction coil. FIG. 12C illustrates deployment of a plurality of implant coils 100C at the identified treatment locations within the highly compliant lower lobe 20B. In particular, deploying may further comprise selecting between implants having high to low austenite final tuning (e.g., low strength to stronger coils) based on the determined tissue compliance. Generally, selecting comprises balancing the determined regional tissue compliance of the portion of lung tissue to a strength of the implant. In this example, selecting may comprise balancing a highly compliant tissue region 20B with implants 100C having a lower austenite final tuning and characterized by a greater strength at body temperature. It will be appreciated that the tissue compliance evaluation methods of the present invention may allow for more safe and efficacious treatment of chronic or reversible obstruction pulmonary disease patients and potentially implantation of fewer coils as the treatment locations may be targeted and/or coil strengths selected based on the tissue compliance evaluation.

In the foregoing specification, the invention is described with reference to specific embodiments thereof, but those skilled in the art will recognize that the invention is not limited thereto. Various features and aspects of the above-described invention can be used individually or jointly. Further, the invention can be utilized in any number of environments and applications beyond those described herein without departing from the broader spirit and scope of the specification. The specification and drawings are, accordingly, to be regarded as illustrative rather than restrictive. It will be recognized that the terms "comprising," "including," and "having," as used herein, are specifically intended to be read as open-ended terms of art.

What is claimed is:

1. A method for treating a lung of a patient with chronic obstructive pulmonary disease, the method comprising:
    determining a regional tissue characteristic of at least a portion of lung tissue of the patient; and
    selecting between a first coil having a first austenite final tuning and a second coil having a second austenite final tuning different than the first austenite final tuning based on the determined regional tissue characteristic of the portion of lung tissue, wherein the first austenite final tuning is characterized by a first transition temperature that is higher than a second transition temperature of the second austenite final tuning.

2. The method of claim 1, wherein the determined regional tissue characteristic comprises a tissue density, strength, or compliance.

3. The method of claim 1, wherein the first and second coils comprise at least one alloy.

4. The method of claim 1, wherein the first transition temperature is just below a body temperature.

5. The method of claim 1, wherein the first transition temperature is in a range from about 30 degrees Celsius to about 35 degrees Celsius.

6. The method of claim 1, wherein the second transition temperature is in a range from about 5 degrees Celsius to about 15 degrees Celsius.

7. The method of claim 1, wherein the second transition temperature is in a range from about 15 degrees Celsius to about 30 degrees Celsius.

8. The method of claim 1, wherein the determining comprises imaging at least the portion of lung tissue of the patient so as to identify a localized lung tissue strength or density.

9. The method of claim 8, wherein imaging comprises taking a computed tomography (CT), magnetic resonance imaging (MRI), optical coherence tomography (OCT), ultrasound, bronchoscopic, or fluoroscopic image of at least the portion of lung tissue of the patient.

10. The method of claim 1, wherein the selecting comprises matching the determined regional tissue characteristic of the portion of lung tissue to a strength of the first or second coil.

11. The method of claim 1, further comprising deploying the selected first or second coil in at least a portion of the lung so as to locally compress lung tissue.

12. The method of claim 1, wherein the determining comprises identifying a first tissue region of lung tissue having a first regional tissue density, and wherein the selecting comprises selecting the first coil for deployment in the first tissue region in response to the first regional tissue density, the method further comprising:
    identifying a second tissue region of the lung having a second regional tissue density different than the first regional tissue density; and
    selecting the second coil for deployment in the second tissue region of the lung in response to the second regional tissue density.

13. The method of claim 12, wherein the first coil has a first coil strength and the second coil has a second coil strength, the first coil strength less than the second coil strength, wherein the determined regional tissue characteristic indicates the first tissue region has a first tissue strength and the second tissue region has a second tissue strength, the first tissue strength less than the second tissue strength, and wherein the second coil strength is sufficiently mismatched to the first tissue strength that deployment of the second coil in the first tissue region would be undesirable.

14. The method of claim 1, wherein the first and second coils are included in a group of candidate coils having differing strengths at body temperature and differing lengths, the method further comprising selecting a subset of the group of candidate coils for deployment in a first tissue region in response to a measurement of a length of the first tissue region, the subset of the group of candidate coils having similar lengths and including the first coil and the second coil.

15. The method of claim 1, wherein chronic obstructive pulmonary disease comprises a disease progression such that the at least a portion of the lung tissue has a first lax tissue volume associated with the determined regional tissue characteristic at a first time and an expected second lax tissue volume greater than the first lax tissue volume at a second time later than the first time, wherein the selecting is performed so that the selected first or second coil, when deployed in the at least a portion of the lung, is configured to compress the first lax tissue volume and to remain strained by the lung tissue at the first time, and is configured to compress the second lax tissue volume at the second time.

16. The method of claim 1, wherein the selecting comprises matching a weaker portion of lung tissue with the first coil having a higher austenite final tuning than the second coil so as to provide a lower tensioning load.

17. The method of claim 16, further comprising delivering the selected first coil having a higher austenite final tuning into the lung of the patient, wherein less force is required to deploy the selected first coil than the second coil.

18. The method of claim 17, wherein the selected first coil is configured to apply a chronic constant force over a longer period of time than the second coil.

19. The method of claim 1, wherein the selecting comprises matching a stronger portion of lung tissue with the second coil having a lower austenite final tuning than the first coil so as to provide a higher tensioning load.

20. The method of claim 1, wherein the selecting further comprises matching a strength of the first or second coil to an implantation location, anatomical characteristic, state of disease, or a state of disease progression.

21. The method of claim 1, wherein the first or second coils comprise at least a nitinol, nickel, or titanium alloy.

22. The method of claim 1, further comprising delivering the selected first or second coil into a portion of the lung of the patient, wherein the selected first or second coil is configured to compress a lung tissue volume.

23. The method of claim 22, further comprising cooling the selected first or second coil below an austenite final temperature prior to or during delivery into the lung of a patient so as to convert the selected first or second coil temporarily to a martensitic metallic phase.

24. A method for treating a lung of a patient with chronic obstructive pulmonary disease, the method comprising:
determining a regional tissue characteristic of at least a portion of lung tissue of the patient, wherein the determining comprises identifying a first tissue region of lung tissue having a first regional tissue density;
selecting between a first coil having a first austenite final tuning and a second coil having a second austenite final tuning different than the first austenite final tuning based on the determined regional tissue characteristic of the portion of lung tissue, wherein the first coil has a first coil strength and the second coil has a second coil strength, the first coil strength less than the second coil strength, and wherein the selecting comprises selecting the first coil for deployment in the first tissue region in response to the first regional tissue density;
identifying a second tissue region of the lung having a second regional tissue density different than the first regional tissue density, wherein the determined regional tissue characteristic indicates the first tissue region has a first tissue strength and the second tissue region has a second tissue strength, the first tissue strength less than the second tissue strength; and
selecting the second coil for deployment in the second tissue region of the lung in response to the second regional tissue density, wherein the second coil strength is sufficiently mismatched to the first tissue strength that deployment of the second coil in the first tissue region would be undesirable.

25. A method for treating a lung of a patient with chronic obstructive pulmonary disease, the method comprising:
determining a regional tissue characteristic of at least a portion of lung tissue of the patient;
selecting between a first coil having a first austenite final tuning and a second coil having a second austenite final tuning different than the first austenite final tuning based on the determined regional tissue characteristic of the portion of lung tissue, wherein the first and second coils are included in a group of candidate coils having differing strengths at body temperature and differing lengths; and
selecting a subset of the group of candidate coils for deployment in a first tissue region in response to a measurement of a length of the first tissue region, the subset of the group of candidate coils having similar lengths and including the first coil and the second coil.

26. The method of claim 25, wherein the first and second coils comprise at least one alloy, wherein the first austenite final tuning is characterized by a first transition temperature that is higher than a second transition temperature of the second austenite final tuning.

27. The method of claim 25, wherein the selecting comprises matching the determined regional tissue characteristic of the portion of lung tissue to a strength of the first or second coil.

28. A method for treating a lung of a patient with chronic obstructive pulmonary disease, the method comprising:
determining a regional tissue characteristic of at least a portion of lung tissue of the patient; and
selecting between a first coil having a first austenite final tuning and a second coil having a second austenite final tuning different than the first austenite final tuning based on the determined regional tissue characteristic of the portion of lung tissue, wherein the selecting comprises matching a weaker portion of lung tissue with the first coil having a higher austenite final tuning than the second coil so as to provide a lower tensioning load.

29. The method of claim 28, further comprising delivering the selected first coil having a higher austenite final tuning into the lung of the patient, wherein less force is required to deploy the selected first coil than the second coil.

30. The method of claim 29, wherein the selected first coil is configured to apply a chronic constant force over a longer period of time than the second coil.

31. The method of claim 28, wherein the first and second coils comprise at least one alloy, wherein the first austenite final tuning is characterized by a first transition temperature that is higher than a second transition temperature of the second austenite final tuning.

32. A method for treating a lung of a patient with chronic obstructive pulmonary disease, the method comprising:

determining a regional tissue characteristic of at least a portion of lung tissue of the patient; and selecting between a first coil having a first austenite final tuning and a second coil having a second austenite final tuning different than the first austenite final tuning based on the determined regional tissue characteristic of the portion of lung tissue, wherein the selecting comprises matching a stronger portion of lung tissue with the second coil having a lower austenite final tuning than the first coil so as to provide a higher tensioning load.

33. The method of claim 32, wherein the first and second coils comprise at least one alloy, wherein the first austenite final tuning is characterized by a first transition temperature that is higher than a second transition temperature of the second austenite final tuning.

* * * * *

UNITED STATES PATENT AND TRADEMARK OFFICE
CERTIFICATE OF CORRECTION

PATENT NO. : 10,390,838 B1  
APPLICATION NO. : 14/831007  
DATED : August 27, 2019  
INVENTOR(S) : Mark Mathis and Verna Rodriguez Page 1 of 1

It is certified that error appears in the above-identified patent and that said Letters Patent is hereby corrected as shown below:

On the Title Page

On page 5, item [56], "Wkipedia," should read -- Wikipedia, --.

In the Specification

Column 17, Line 20, "the brochoscope" should read -- the bronchoscope --.

Signed and Sealed this  
Twenty-sixth Day of November, 2019

Andrei Iancu  
*Director of the United States Patent and Trademark Office*